US009835629B2

(12) United States Patent
Rogers et al.

(10) Patent No.: US 9,835,629 B2
(45) Date of Patent: Dec. 5, 2017

(54) METHODS AND REAGENTS FOR BIOMOLECULE LABELING, ENRICHMENT AND GENTLE ELUTION

(71) Applicant: Pierce Biotechnology, Inc., Rockford, IL (US)

(72) Inventors: John Charles Rogers, Rockton, IL (US); Ryan Daniel Bomgarden, Winnebago, IL (US); Christopher Laurence Etienne, Fitchburg, WI (US); Eric Leigh Hommema, Roscoe, IL (US)

(73) Assignee: Pierce Biotechnology, Inc., Rockford, IL (US)

( * ) Notice: Subject to any disclaimer, the term of this patent is extended or adjusted under 35 U.S.C. 154(b) by 488 days.

(21) Appl. No.: 13/794,248

(22) Filed: Mar. 11, 2013

(65) Prior Publication Data

US 2013/0309689 A1  Nov. 21, 2013

Related U.S. Application Data

(60) Provisional application No. 61/648,959, filed on May 18, 2012.

(51) Int. Cl.
*G01N 33/68* (2006.01)
*G01N 33/58* (2006.01)

(52) U.S. Cl.
CPC ......... *G01N 33/6848* (2013.01); *G01N 33/58* (2013.01); *G01N 33/6803* (2013.01)

(58) Field of Classification Search
None
See application file for complete search history.

(56) References Cited

U.S. PATENT DOCUMENTS

| | | | |
|---|---|---|---|
| 5,112,951 A | 5/1992 | Beidler | |
| 5,258,507 A | 11/1993 | Cruickshank | |
| 5,726,293 A | 3/1998 | Seed | |
| 7,001,738 B2 | 2/2006 | Snyder et al. | |
| 7,932,388 B2 | 4/2011 | Pappin et al. | |
| 2008/0193915 A1* | 8/2008 | Prokai et al. | 435/5 |
| 2008/0255004 A1 | 10/2008 | Neurauter et al. | |
| 2010/0178710 A1* | 7/2010 | Hamon et al. | 436/173 |

OTHER PUBLICATIONS

Ryan D. Bomgarden, Rosa I. Viner, Karsten Kuhn, Ian Pike and John Rogers, "Iodoacetyl Tandem Mass Tags for Cysteine Peptide Modification, Enrichment and Quantitation," created/modified on Internet May 15, 2012.*
Thermo Scientific Instructions "TMT® Mass Tagging Kits and Reagents," pp. 1-10, created/modified on Internet Jan. 23, 2012.*
Nühse et al., "Unit 18.13 Isolation of Phosphopeptides by Immobilized Metal Ion Affinity Chromatography," Current Protocols in Molecular Biology, Published Online: Jan. 1, 2007, pp. 18.13.1-18. 13.23.*
Haugland, "A Guide to Fluorescent Probes and Labeling Technologies," Tenth Edition, 2005, pp. 95-116.*
Sigma-90358, "Triethylammonium acetate buffer," retrieved from http://www.sigmaaldrich.com/catalog/product/sigma/90358?lang=en&region=US on Mar. 22, 2017.*
Feng et al. Quantitative Proteomic Profiling of Muscle Type-Dependent and Age-Dependent Protein Carbonylation in Rat Skeletal Muscle Mitochondria. J Gerontol A Biol Sci Med Sci. vol. 63, No. 11 (2008), pp. 1137-1152.
Gardner and Brodbelt. Preferential Cleavage of N—N Hydrazone Bonds for Sequencing Bis-arylhydrazone Conjugated Peptides by Electron Transfer Dissociation. Anal. Chem. vol. 82 (2010), pp. 5751-5759, Supporting information (11 pages).
Kidd et al. Profiling Serine Hydrolase Activities in Complex Proteomes. Biochemistry vol. 40 (2001), pp. 4005-4010.
Muller et al. Isotope-Tagged Cross-Linking Reagents. A New Tool in Mass Spectrometric Protein Interaction Analysis. Anal. Chem. vol. 73 (2001), pp. 1927-1934.
Pichler et al. Peptide Labeling with Isobaric Tags Yields Higher Identification Rates Using iTRAQ 4-Plex Compared to TMT 6-Plex and iTRAQ 8-Plex on LTQ Orbitrap. Anal. Chem. vol. 82 (2010), pp. 6549-6558.
Tang and Bruce. Chemical Cross-Linking for Protein-Protein Interaction Studies. Mass Spectrometry of Proteins and Peptides, vol. 492 (2009), pp. 283-293.
Wu et al. Mass Spectrometric Determination of Disulfide Linkages in Recombinant Therapeutic Proteins Using On-line LC-MS with Electron Transfer Dissociation (ETD). Anal Chem. vol. 81 (2009), pp. 112-122.
Xu and Chance. Hydroxyl Radical-Mediated Modification of Proteins as Probes for Structural Proteomics. Chem. Rev. vol. 107 (2007), pp. 3514-3543.
Thermo Scientific Instructions, "Immobilized Anti-TMT™ Resin & TMT Elution Buffer," Product Numbers 90076 and 90104, Oct. 15, 2012, 4 pages.

* cited by examiner

*Primary Examiner* — Galina Yakovleva

(57) ABSTRACT

Methods and sets of non-biological reagents (elution reagents, tag isomers, tag reactive groups, crosslinkers) for single or multiplexed capture and gentle elution of biomolecules. Examples are provided using amine- and cysteine-reactive reagents for enrichment of proteins, peptides, and rare peptide modifications.

21 Claims, 31 Drawing Sheets
(21 of 31 Drawing Sheet(s) Filed in Color)

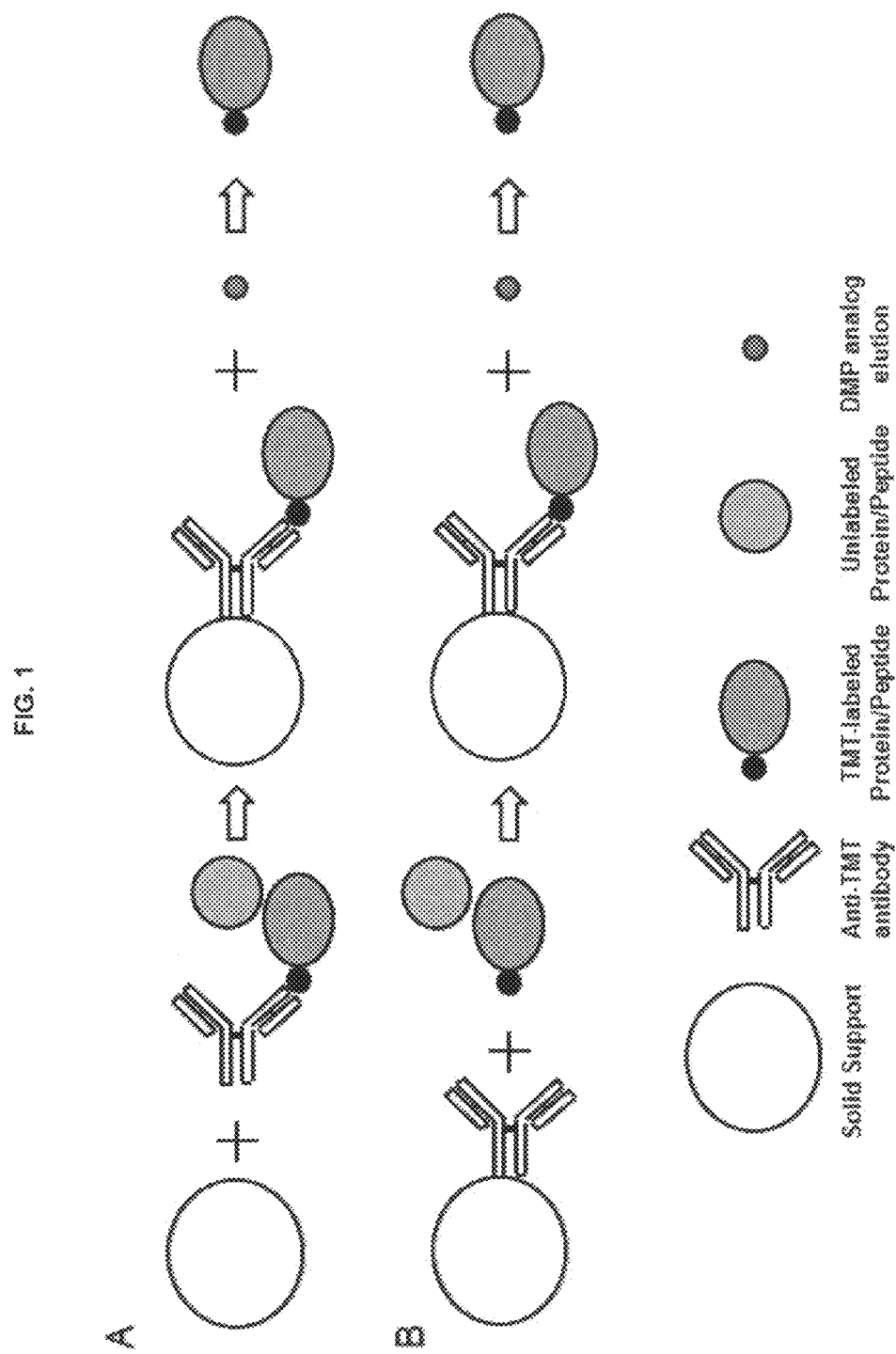

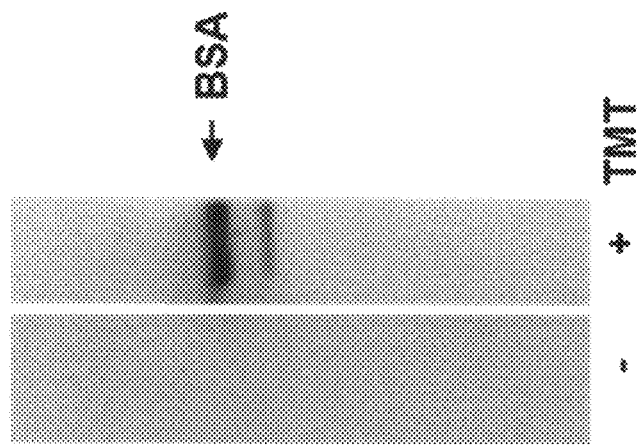

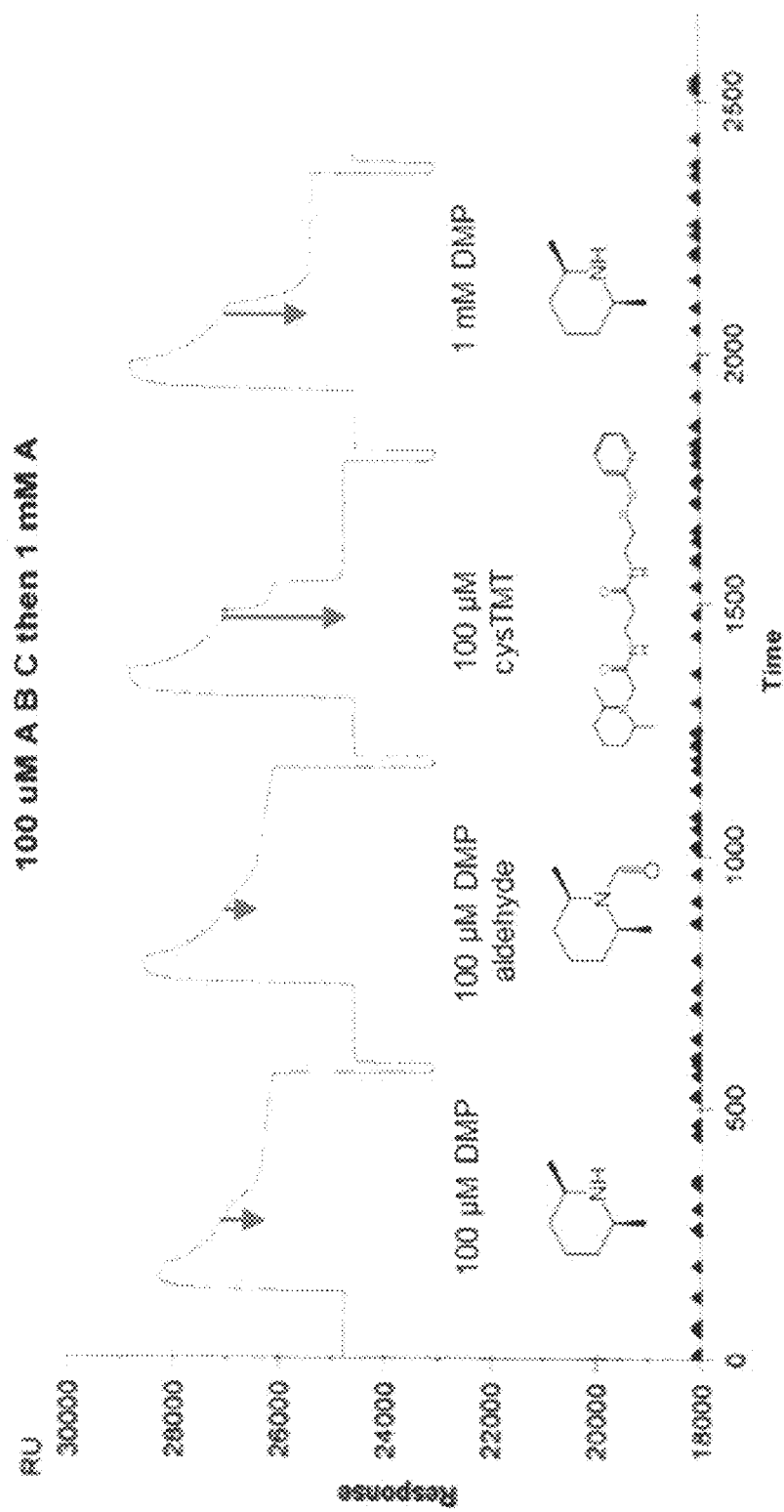

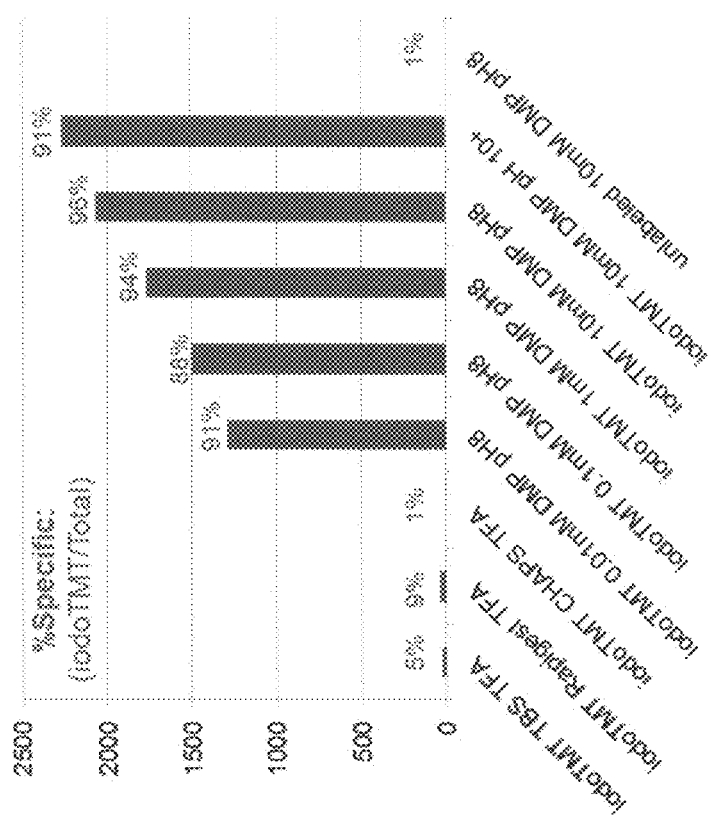

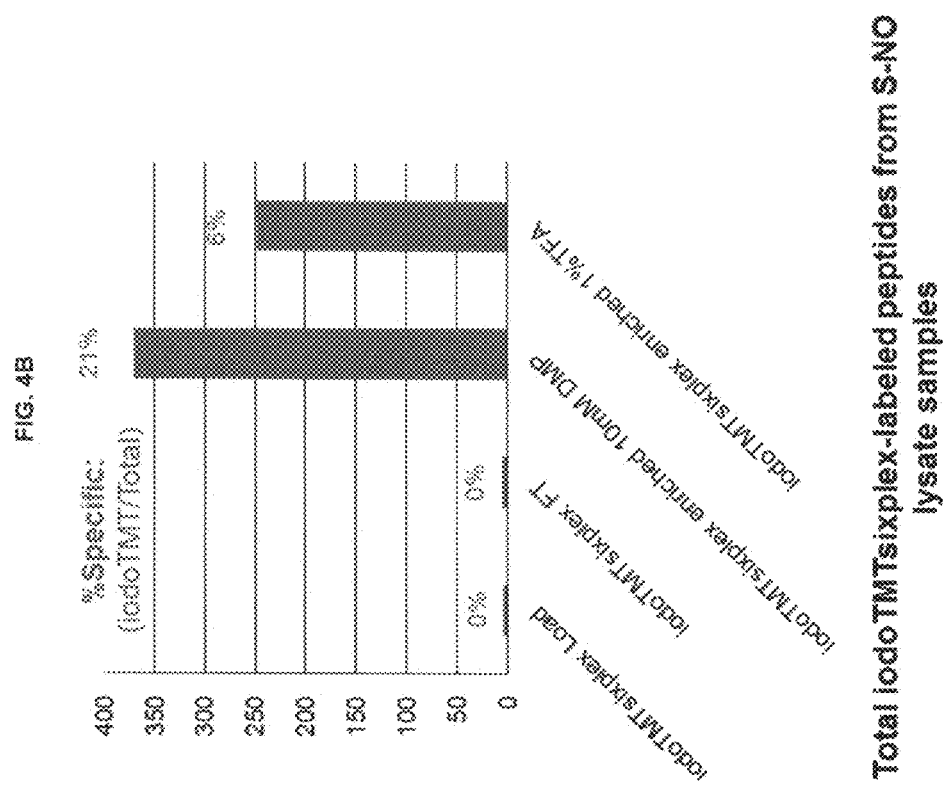

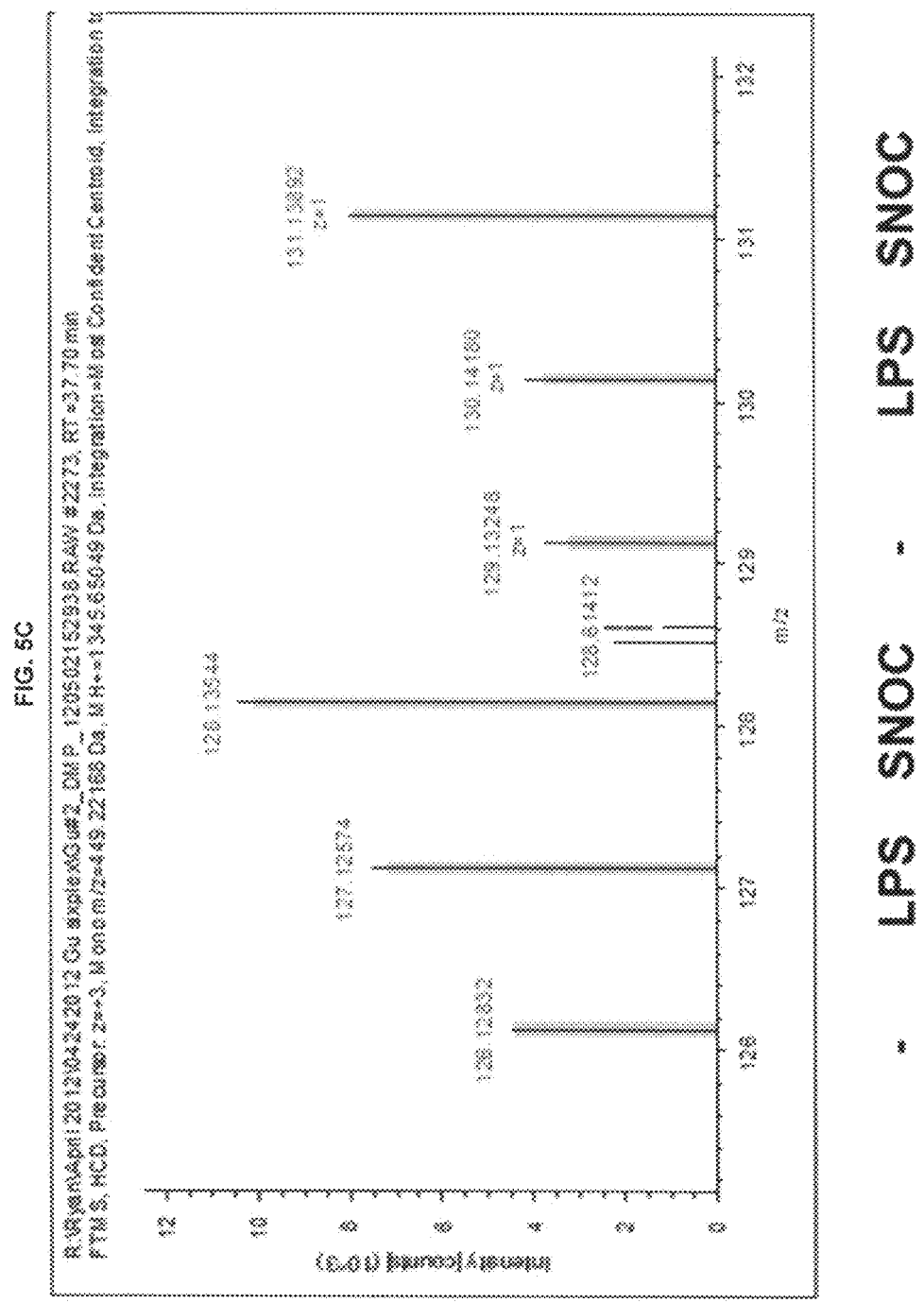

FIG. 6
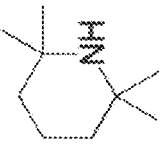 2,2,4,4-tetramethyl piperidine
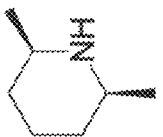 cis-2,6-dimethyl piperidine
 2-methyl piperidine
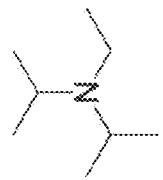 Diisopropylethylamine (DIPEA)
 Triethylamine (TEA)
2-S-methyl piperidine
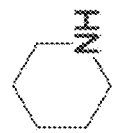 Piperidine

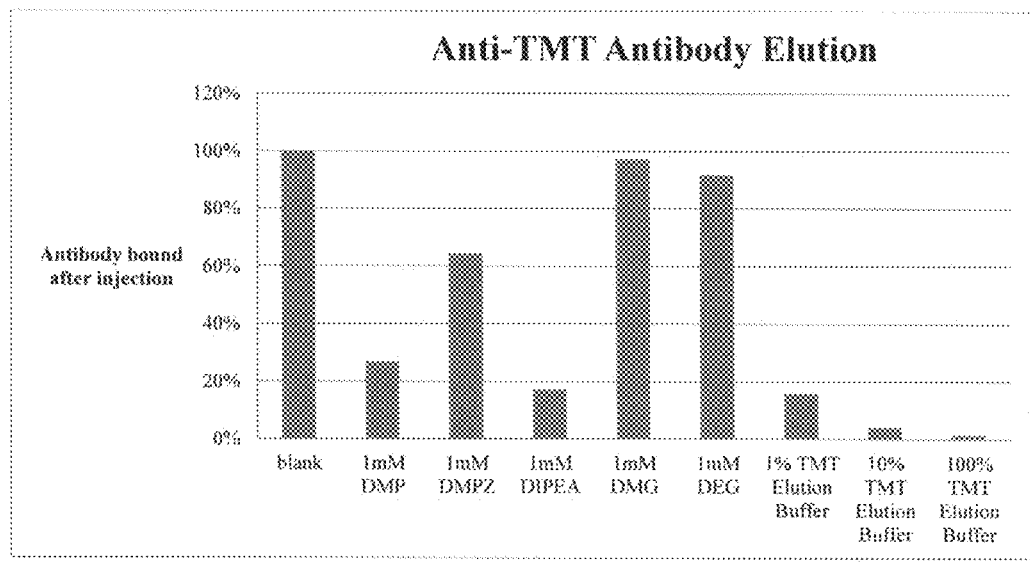

FIG. 8A
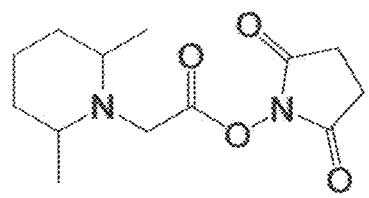
DMP-NHS
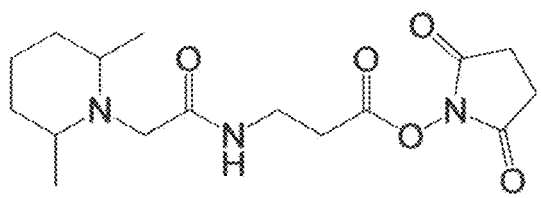
TMT
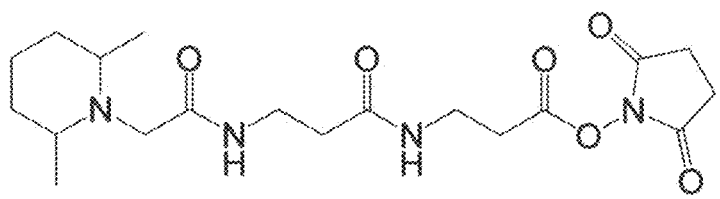
TMT-βala
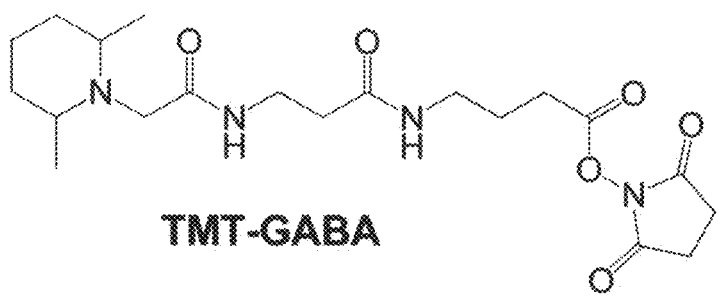
TMT-GABA
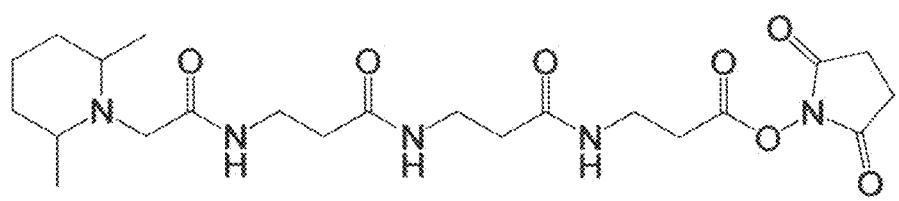
TMT-βalaβala

FIG. 8B
¹³C-Variant
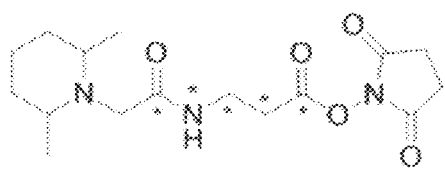
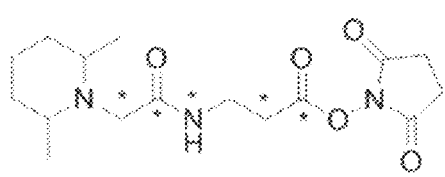
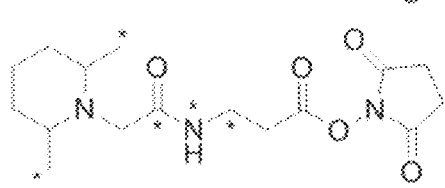
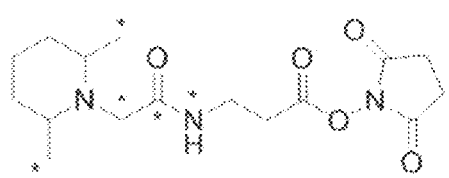
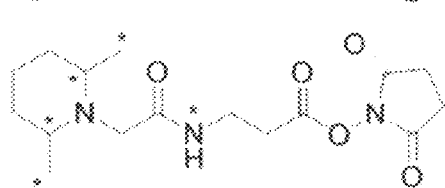
¹⁵N-Variant
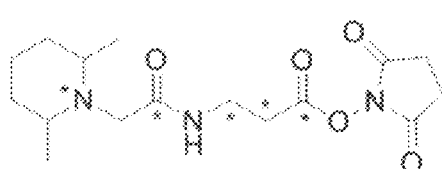
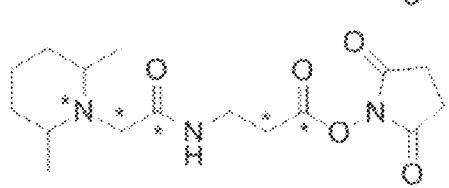
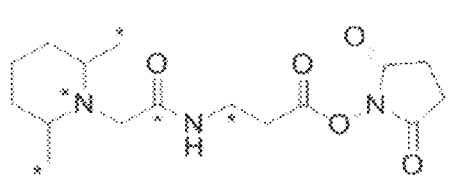
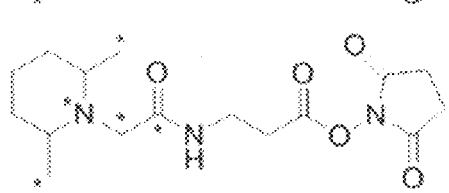

FIG. 11
Thermo Scientific cysTMTzero Reagent
for Method Development & Duplex Isotopic Quantitation
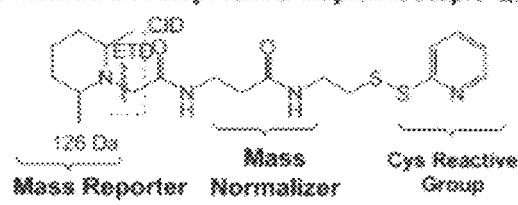
126 Da — Mass Reporter | Mass Normalizer | Cys Reactive Group
Thermo Scientific cysTMTsixplex Reagents
for Sixplex Isobaric Quantitation
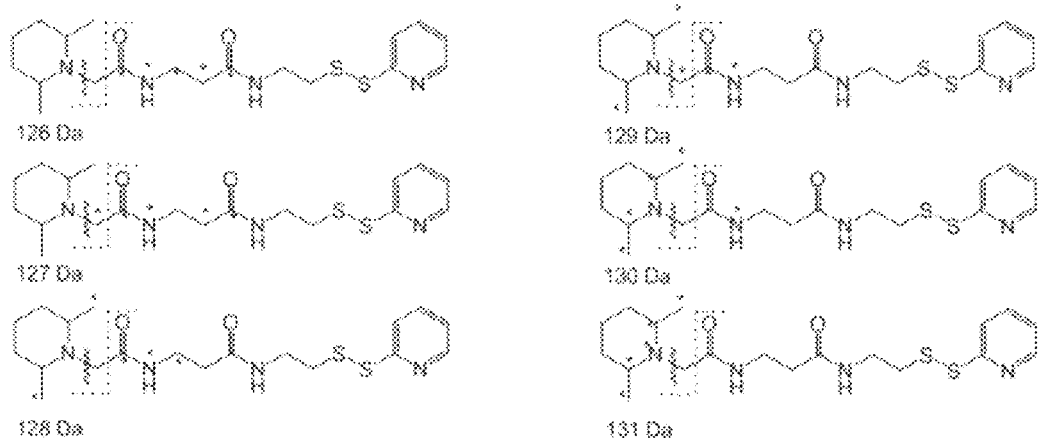
126 Da  129 Da
127 Da  130 Da
128 Da  131 Da FIG. 20
oxyTMTzero
Method Development & Duplex Isotopic Quantitation
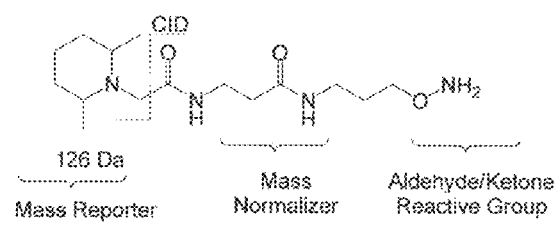
126 Da — Mass Reporter
Mass Normalizer
Aldehyde/Ketone Reactive Group
oxyTMTsixplex
Six Plex Isobaric Quantitation
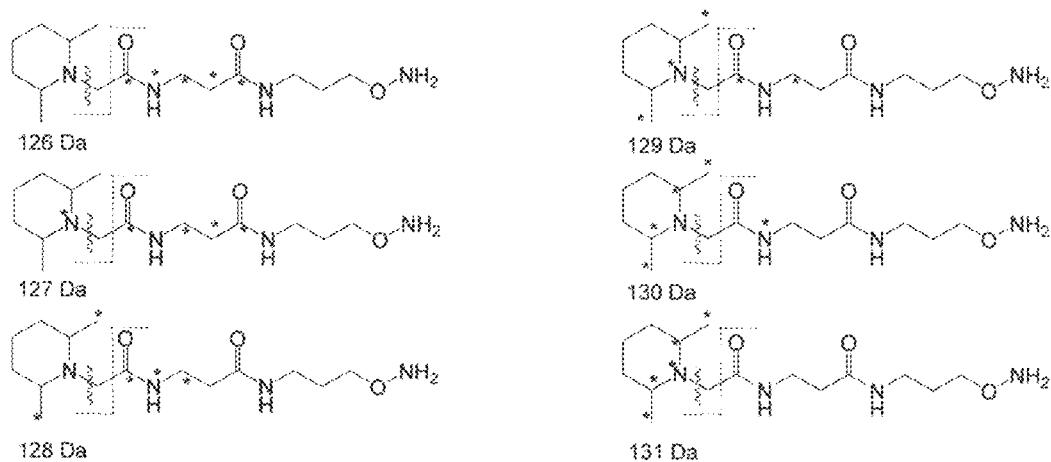
126 Da
127 Da
128 Da
129 Da
130 Da
131 Da

FIG. 21
hydrazideTMTzero
Method Development & Duplex Isotopic Quantitation
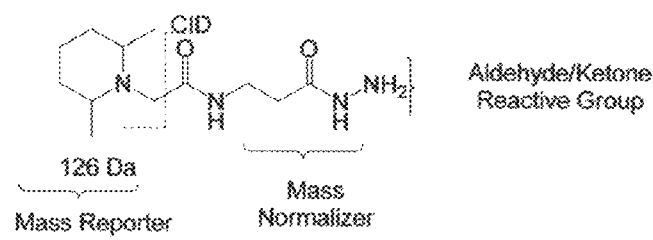
hydrazideTMTsixplex
Six Plex Isobaric Quantitation
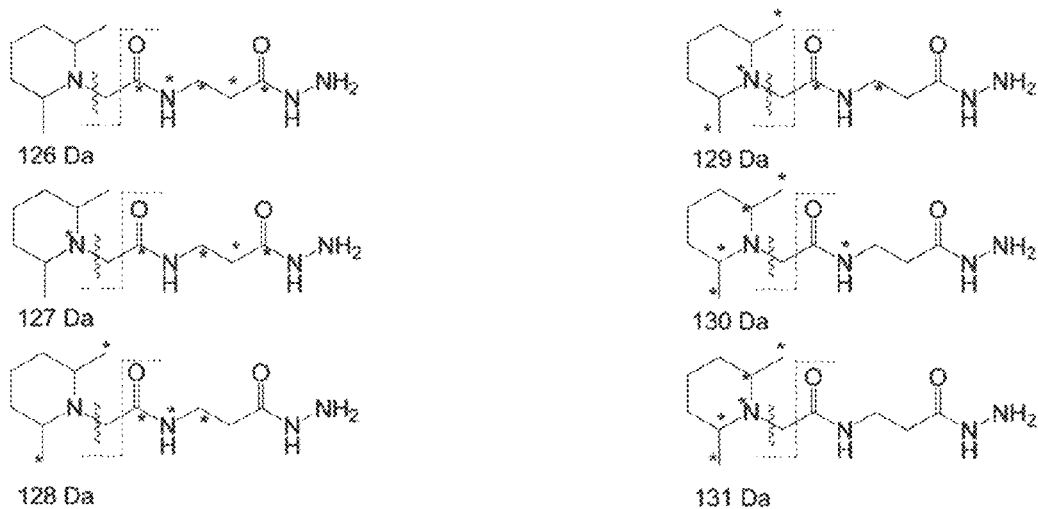

METHODS AND REAGENTS FOR BIOMOLECULE LABELING, ENRICHMENT AND GENTLE ELUTION

CROSS REFERENCE TO RELATED APPLICATIONS

This application claims priority to U.S. application Ser. No. 61/648,959 filed May 18, 2012 which is expressly incorporated by reference herein in its entirety.

SUMMARY

Methods and reagents for labeling, selective enrichment, and gentle elution of captured biomolecules. The method affinity tags a biological molecule for its selective capture and enrichment in multiplex applications. The biological molecule can be a cell, protein, peptide, nucleic acid, oligosaccharide, glycoprotein, lipid, carbohydrate, hormone, and/or toxin, or derivatives of these. The method and reagents selectively label amine, carboxyl, thiol, carbonyl (aldehyde/ketone), azide, alkyne, cyclic alkyne, and phosphine reactive groups, and thus selectively labels proteins, peptides, glycans, steroids, nucleotides, lipids, and/or small metabolites.

The method used multiplexed antibody-based capture of a series of isomers or isotopically labeled variants of dimethyl piperidine- or dimethyl piperazine, collectively DMP-, based chemical affinity tags. The DMP tags are detection and capture bioconjugation reagents; they contain a small, non-biological epitope at one end of the tag, and a reactive group at the other end of the tag. The DMP tags are strong antigens for antibodies that are developed against the epitope on the affinity tag. The antibodies are immobilized, and labeled samples are captured with the immobilized antibody. The labeled samples are then washed and competitively eluted under native conditions, e.g. in the absence of a detergent such as sodium dodecyl sulfate or a denaturant such as urea, i.e. gentle elution, with a small molecule version of the epitope which is comprised of the tag itself or a fragment, substructure, or structural analog of the epitope. The elution reagent is removed by methods known in the art, e.g., vacuum drying, desalting with dialysis or reversed phase or size exclusion chromatography. Multiple versions of the chemical tags are constructed with heavy stable isotopes and/or unique linkers between the epitope and reactive groups, allowing labeling of multiple samples, mixing of these samples, and multiplexed capture prior to mass spectrometry analysis. The reactive groups specifically label amine, carboxyls, carbonyls, azides, phosphines, alkynes, or cyclic alkynes. The competitive elution reagent may be removed by dialysis, size-exclusion desalting resin, precipitation, or vacuum drying.

The method selectively captures one or more structural analogs (e.g. β-Ala) or isotopically-labeled isomers of a DMP tag in a single or multiplexed capture reaction from a biological matrix using an antibody that is epitope-selective, i.e., dimethyl piperidine-selective and analogs thereof.

BACKGROUND

Biomolecules, including protein, peptide, nucleic acid, oligosaccharide, glycoprotein, lipid, carbohydrate, hormones, toxins, and cells are studied by multiple analytical methods to determine their structure and function, to characterize any modifications and the effects of these modifications (e.g. structure-function relationships), and to quantify changes in the biomolecule levels and their interactions in response to growth, development, disease, treatment, and other environmental factors. These biomolecules may be present in the environment, in blood or serum, in tissue, in cells, in subcellular compartments, and/or in cellular complexes.

Many reagents and research tools have been developed to enrich biomolecules of interest for these studies. These reagents include biotin, desthiobiotin, nitrophenyl reagents, and other bioconjugation derivatives. In one example, a biomolecule is conjugated with a biotin reagent ("bait"), added to a complex sample, and then captured through the substantially irreversible $10^{-14}$ mol/L binding interaction with streptavidin-coated beads or surfaces to co-enrich other molecules ("prey") that may bind or interact with the bait molecule. In another example, an antibody is conjugated with a biotinylating reagent so that it may be captured with an immobilized biotin-binding protein. The antibody is then added to a biological sample, wherein a target antigen is then captured from the complex protein sample with streptavidin-coated beads or surfaces for characterization or quantification.

Prior to elution of bound material, particles may be washed with non-denaturing detergents, high or low salt, pH, or solvents to reduce nonspecific background, and then the antigen can be eluted with strong acidic or basic pH conditions or denaturing concentrations of detergent. In one example, a biotinylated protein or peptide can be enriched with streptavidin coated beads, but can only be recovered through heating at 90° C. in combination with acidic buffers, organic solvents, strong detergents, and excess competitive biotin. Desthiobiotin, iminobiotin, monomeric avidin, and nitrosylated streptavidin are all reagents with lower affinity interactions, but these still require heat, extreme pH, and/or other harsh elution conditions to recover biotinylated proteins or peptides efficiently. This strategy will also capture endogenously biotinylated molecules, which may interfere with the analysis.

Alternatively, fusion proteins are expressed with N- or C-terminal affinity tags, such as 6xHis, FLAG, glutathione S-transferase (GST), or hemagglutinin (HA). Each of these tags can be captured with affinity resins to purify expressed fusion proteins. In one example, a protein with a 6xHis tag can be captured through the strong interaction between the imidazole ring on histidine residues in the affinity tag and a nickel or cobalt chelated immobilized metal affinity column (IMAC). This interaction is not affected by denaturing conditions, allowing aggregates of His-tagged protein to be solubilized in 8M urea denaturing conditions, captured with Ni- or Co-IMAC, refolded on column by reducing the urea concentration, and then competitively eluted with imidazole. In another example, a fusion protein expressed with GST, FLAG, or HA affinity tag can be purified with glutathione resin or immobilized anti-FLAG or anti-HA antibody resins, respectively, and then competitively eluted with free glutathione, FLAG peptide, or HA peptide. When the antigen of interest is present at a very low concentration in a complex sample, competitive and selective elution conditions may be necessary to reduce the background of non-specific biomolecules that may co-elute under harsh or denaturing conditions. Competitive elution conditions improve the quantitative recovery of the analyte and the specificity of elution of biomolecules.

The analysis of rare protein modifications and of protein-protein interactions is complicated by the low stoichiometry and transient nature of the interactions. In addition, while many modifications and interactions may be detected by antibody-based methods, the exact location and molecular characterization of these modifications or interactions are difficult to study. In one example, a protein may be nitrosylated on cysteine residues in response to oxidative stress or other environmental stimuli. While it is possible to use chemical methods to specifically biotinylate nitrosylated sites using a "biotin-switch" methodology, and antibody-based methods to capture a protein of interest and detect the presence of nitrosylation, it is very difficult to identify the site of modification and quantitatively monitor the site-specific changes under different treatment conditions or over time.

Similarly, a protein-protein interaction can be inferred by the co-immunocapture of a prey protein with a bait protein, but the molecular details of this interaction are missing without a chemical means of tagging the precise sites of interaction. In one example, a homobifunctional, amine-reactive chemical crosslinker is added to a cell lysate, a protein of interest is captured with an antibody to that protein, and other proteins that were co-enriched are assessed by resolving the enriched sample electrophoretically on a denaturing polyacrylamide gel, transferring the lane of separated proteins to a membrane, and then probing this membrane with an antibody against candidate proteins by Western blot to detect interaction and co-enrichment. In another example, the crosslinker may contain an affinity handle so that the sample may be digested and the cross-linked fragments may be enriched with the affinity handle to allow identification of the cross-linked fragments and their sites of linkage. Reagents that allow enrichment and quantitative analysis of these modifications and interactions may provide critical understanding of protein structure and interactions.

The efficiency of capture depends upon the affinity of the binding interaction, the presence of interfering molecules, and the accessibility of the binding components. Accessibility may be affected by protein folding, aggregation, complexes, and incomplete solubilization. In one example, an antibody is used to capture a protein antigen from a cell lysate. The efficiency of capture is determined in a complementary assay, such as ELISA or Western blot, by comparing samples of the starting lysate, the captured protein sample, and the depleted lysate. Because capture or depletion is often incomplete, reagent controls may be used to account for differences in capture efficiency between conditions. In one example, a version of the targeted protein is expressed or tagged with a unique dye, isotopic signature, or other modification and then spiked into all samples, captured along with the native target of interest, and then quantified to assess and normalize capture efficiency across all samples. In a similar example, multiple samples from multiple conditions are modified with a set of similar but distinct tags, the uniquely tagged samples are combined, the antigens are captured simultaneously in one reaction, and then the relative intensities of the unique tags are quantified after elution to compare protein amounts. This multiplexed capture strategy allows many samples to be enriched and analyzed simultaneously from one capture experiment. This strategy reduces the variability introduced with separate capture and elution experiments.

It is often desirable to elute a captured biomolecule or captured cell in its native form in order to preserve structural features, enzymatic function, or cellular viability. In one example, a biomolecule may be labeled with a modified biotin reagent, such as desthiobiotin, and/or captured with a modified biotin binding protein, such as monomeric avidin, which have a lower binding affinity than the native avidin-biotin interaction. After capture, the bound biomolecule may be competitively eluted with free biotin. Despite the lower affinity, this binding interaction is cooperative and high affinity, making it difficult to dissociate with high recovery without heat or extreme pH conditions. An elution reagent that can quickly and efficiently elute captured molecules under gentle conditions may better preserve the target analyte structure and function.

Similarly, after capture and elution of a molecule, it is often desirable to remove or neutralize the elution reagent without affecting sample quality or recovery. In one example, a desthiobiotin-labeled sample may be eluted from streptavidin with a solution of sodium dodecyl sulfate (SDS), a strong denaturing detergent. In some analyses, such as Western blotting, this detergent may be advantageous for solubilization and denaturation. However, in other analyses, such as mass spectrometric analysis, even low quantities of this detergent can prevent detection of the analyte and cause deterioration of the instrument performance. For standard liquid chromatography-mass spectrometric (LC-MS) analysis, it is often necessary to neutralize and remove the elution reagent in order to avoid interferences and the need to replace chromatography consumables and/or repair instrumentation.

BRIEF DESCRIPTION OF THE DRAWINGS

The patent or application file contains at least one drawing executed in color. A Petition under 37 C.F.R. §1.84 requesting acceptance of the color drawing is being filed separately. Copies of this patent or patent application publication with color drawing(s) will be provided by the Office upon request and payment of the necessary fee.

FIG. 1 illustrates modes of antibody binding and elution.

FIGS. 2A-D show results of antibody characterization.

FIGS. 3A-B show specificity of elution.

FIGS. 4A-B show enrichment of total (FIG. 4A) and S-nitrosylated cysteine (FIG. 4B) peptides.

FIGS. 5A-C show multiplexed enrichment, identification, localization of modification, and quantitation of S-nitrosylated peptides.

FIG. 6 are chemical structures of piperidine elution reagents.

FIGS. 7A-B show anti-TMT™ antibody elution by piperidine elution reagents.

FIGS. 8A-B are chemical structures of isomers and isotopomers.

FIG. 11 are chemical structures for cysteine-reactive tandem mass tags (cysTMT™) labeling.

FIG. 20 shows chemical structures for alkoxyamine tandem mass tags (oxyTMT™) labeling.

FIG. 21 shows chemical structures for hydrazide tandem mass tags (hydrazideTMT™) labeling.

DETAILED DESCRIPTION

Figure 2A:
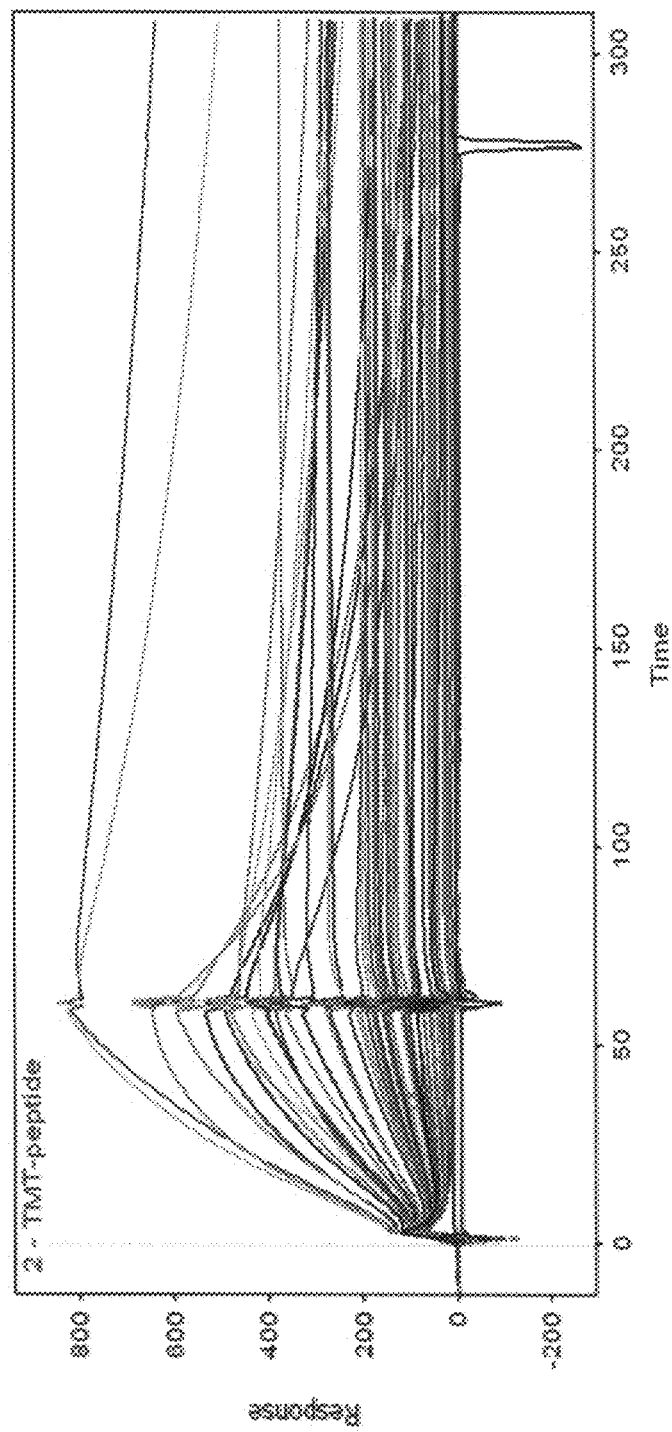

One embodiment is a method for labeling and selective enrichment of a biomolecule in a sample. The method (a) covalently tags a biomolecule in the sample with at least one dimethyl piperidine- or dimethyl piperazine- (DMP-) based chemical affinity tag under conditions to result in a DMP-based chemically tagged biomolecule, (b) then selectively captures the DMP-based chemically tagged biomolecule with either (i) a solid support to which a DMP epitope or analog thereof-selective antibody is attached, or (ii) a solution of a DMP epitope or analog thereof-selective antibody, and then contacting the solution with a solid support capable of capturing the DMP epitope or analog thereof-selective antibody to selectively capture the DMP-based chemically tagged biomolecule, and (c) eluting the DMP-based chemically tagged biomolecule by adding at least one elution reagent comprising a displacement molecule to the solid support to competitively selectively elute under native conditions an intact DMP-based chemically affinity tagged biomolecule.

In one embodiment, the method reversibly captures a biomolecule labeled with an N-substituted piperidine compound or a salt thereof. The N-substituted piperidine has the following structure,

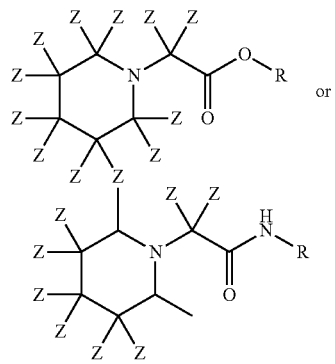

where R is any length linker comprised of C, N, O, H between the N-substituted ring and the reactive group(s); and where each Z is independently hydrogen, fluorine, chlorine, bromine, iodine, an amino acid side chain, a straight chain or branched $C_1$-$C_6$ alkyl group that may optionally contain a substituted or unsubstituted aryl group where the carbon atoms of the alkyl and aryl groups each independently comprise hydrogen or fluorine atoms; a straight chain or branched $C_1$-$C_6$ alkyl ether group that may optionally contain a substituted or unsubstituted aryl group where the carbon atoms of the alkyl and aryl groups each independently comprise hydrogen or fluorine atoms; or a straight chain or branched $C_1$-$C_6$ alkoxy group that may optionally contain a substituted or unsubstituted aryl group wherein the carbon atoms of the alkyl and aryl groups each independently comprise hydrogen or fluorine atoms. The method (a) covalently tags a biomolecule in the sample with at least one N-substituted piperidine compound or a salt thereof-based chemical affinity tag under conditions to result in a N-substituted piperidine compound or a salt thereof-based chemically tagged biomolecule, (b) selectively captures the N-substituted piperidine or a salt thereof based chemically tagged biomolecule with either (i) a solid support to which an N-substituted piperidine compound or a salt thereof epitope or analog thereof-selective antibody is attached, or (ii) a solution comprising an N-substituted piperidine compound or a salt thereof epitope or analog thereof-selective antibody, and then contacting the solution with a solid support capable of capturing the N-substituted piperidine compound or a salt thereof epitope or analog thereof-selective antibody to selectively capture the N-substituted piperidine compound or a salt thereof-based chemically tagged biomolecule, and (c) elutes the N-substituted piperidine compound or a salt thereof-based chemically tagged biomolecule by adding at least one elution reagent comprising at least one displacement molecule to the solid support to competitively selectively elute under native conditions an intact N-substituted piperidine compound or a salt thereof-based chemically affinity tagged biomolecule.

In one embodiment, the N-substituted piperidine compound or a salt thereof-based chemically affinity tagged biomolecule is a DMP-based chemical affinity tag.

In one embodiment, at least one displacement molecule in step (c) is a substructure of the DMP epitope or analog thereof. In embodiments, step (a) is performed on a single sample, or step (a) is performed on at least two separate samples and the separate samples are combined prior to step (b) resulting in a multiplex method.

In one embodiment, the DMP-based chemical affinity tag is among the compounds of FIG. 7 and structural analogs thereof and among the compounds of FIG. 8 and structural analogs thereof, where the DMP-based chemical affinity tag is optionally isotopically labeled. In one embodiment, the DMP-based affinity tag has a linking group and a reactive group, where the DMP-based chemical affinity tag labels the biomolecule by at least one of amine, carboxyl, thiol, carbonyl (aldehyde/ketone), azide, alkyne, cyclic alkyne, and/or phosphine reactive chemistries.

In one embodiment, the elution of step (c) occurs at pH ranging from about 4 to about 10. In contrast, biotin-containing capture reagents such as ICAT require elution at pH less than 4

In one embodiment, the method further comprises, after step (c), a step (d) where the elution reagent(s) are removed by vacuum drying or desalting with dialysis or reversed phase or size exclusion chromatography. The elution reagents are volatile, and thus are readily removed by, e.g., vacuum drying.

In embodiments, the biomolecule(s) tagged is/are cells, proteins, peptides, glycans, steroids, nucleotides, sugars, toxins, lipids, and/or small metabolites.

In one embodiment, the elution reagent contains at least one displacement molecule. In one embodiment, the displacement molecule(s) is a substructure of the DMP epitope and epitope analogs. In one embodiment, the displacement molecule is piperidine, 2-S-methyl piperidine, 2-methyl piperidine, cis 2,6-dimethyl piperidine, 2,2,4,4-tetramethyl piperidine, triethylamine, and/or diisopropylethylamine. In one embodiment, the displacement molecule is not a substructure of the DMP epitope and epitope analogs. In one embodiment, the displacement molecule is triethylamine (TEA), N,N-diisopropylethylamine (DIPEA), triethylammonium acetate (TEAA), and/or triethylammonium bicarbonate (TEAB). In one embodiment, the elution reagent comprises more than one displacement molecule, where the displacement molecules may be a combination of a substructure of the DMP epitope and epitope analogs, a combination of compounds that are not a substructure of the DMP epitope and epitope analogs, and combinations of substructure of the DMP epitope and epitope analogs and compounds that are not a substructure of the DMP epitope and epitope analogs. In one embodiment, the elution reagent contains at least one buffer, e.g., ((hydroxymethyl)aminomethane) (Tris), 4-(2-hydroxyethyl)-1-piperazineethanesulfonic acid (HEPES), 2-[[1,3-dihydroxy-2-(hydroxymethyl)propan-2-yl]amino]ethanesulfonic acid (TES), phosphate, 2-(N-morpholino)ethanesulfonic acid (MES), 3-morpholinopropane-1-sulfonic acid (MOPS), 1,4-piperazinediethanesulfonic acid (PIPES), bicarbonate, carbonate, N-(2-hydroxy-1,1-bis(hydroxymethyl)ethyl)glycine (tricine), N,N-(bis(2-hydroxyethyl)glycine (bicine), triethylammonium acetate (TEAA), and/or triethylammonium bicarbonate (TEAB), etc.

In one embodiment, the DMP epitope-selective antibody in step (b) is a glycoform, Fab fragment, or derivative thereof. In addition, the DMP epitope to which the described antibody reacts and is present in step (b) of the method can be a fragment, substructure, structural analog, or a derivative of the DMP-based affinity tag.

In embodiments, the DMP-based chemical affinity tag added in step (a) optionally contains a crosslinker.

In one embodiment, the method further comprises after the elution of step (c) or after the removal of elution reagent in step (d), performing mass spectroscopy analysis on the eluted biomolecule.

In embodiments, the solid support of step (b) is a particle, e.g., a magnetic particle, and/or uses a plastic, glass, ceramics, silicone, metal, and/or cellulose surface.

In one embodiment, the method may further add at least a second DMP-based chemical affinity tag to the sample, different from the first DMP-based affinity tag.

In one embodiment of the method, the DMP-based chemical affinity tag has the piperidine structure

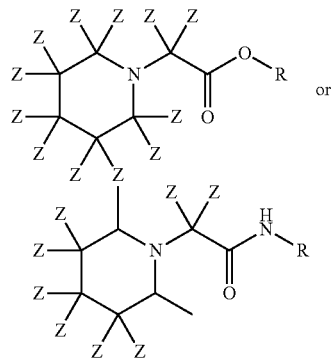

where R is any length linker comprised of C, N, O, H between the N-substituted ring and the reactive group(s); and where each Z is independently hydrogen, fluorine, chlorine, bromine, iodine, an amino acid side chain, a straight chain or branched $C_1$-$C_6$ alkyl group that may optionally contain a substituted or unsubstituted aryl group wherein the carbon atoms of the alkyl and aryl groups each independently comprise hydrogen or fluorine atoms, a straight chain or branched $C_1$-$C_6$ alkyl ether group that may optionally contain a substituted or unsubstituted aryl group wherein the carbon atoms of the alkyl and aryl groups each independently comprise hydrogen or fluorine atoms, or a straight chain or branched $C_1$-$C_6$ alkoxy group that may optionally contain a substituted or unsubstituted aryl group where the carbon atoms of the alkyl and aryl groups each independently comprise hydrogen or fluorine atoms.

In one embodiment, the displacement molecule in step (c) is sufficiently soluble to permit competitive elution with a concentration 10 to 1,000,000,000 times the affinity binding constant of the DMP epitope or analog thereof selective antibody affinity to the DMP-based chemical affinity tag. In one embodiment, step (c) is performed at a pH in the range of about 4 to about 10.

In one embodiment, the method (a) covalently tags a biomolecule in the sample with at least one dimethyl piperazine- (DMPZ-) based chemical affinity tag under conditions to result in a DMPZ-based chemically tagged biomolecule, (b) selectively captures the DMPZ-based chemically tagged biomolecule with either (i) a solid support to which a DMPZ epitope or analog thereof-selective antibody is attached, or (ii) a solution comprising a DMPZ epitope or analog thereof-selective antibody, and thereafter contacting the solution with a solid support capable of capturing the DMPZ epitope or analog thereof-selective antibody to selectively capture the DMPZ-based chemically tagged biomolecule, and (c) elutes the DMPZ-based chemically tagged biomolecule by adding at least one elution reagent comprising at least one displacement molecule to the solid support to competitively selectively elute under native conditions an intact DMPZ-based chemically tagged biomolecule.

In one embodiment, the method reversibly captures a biomolecule labeled with an N-substituted piperazine compound or a salt thereof having the following structure

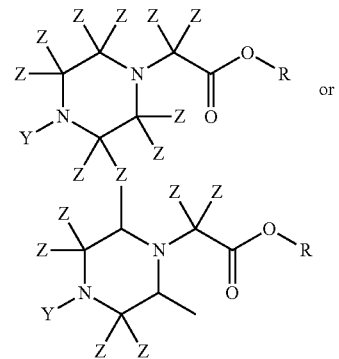

where Y is a straight chain or branched $C_1$-$C_6$ alkyl group or a straight chain or branched $C_1$-$C_6$ alkyl ether group, where the carbon atoms of the alkyl group or alkyl ether group each independently comprise hydrogen, deuterium or fluorine atoms; where R is any length linker comprised of C, N, O, H between the N-substituted ring and the reactive group(s); and where each Z is independently hydrogen, fluorine, chlorine, bromine, iodine, an amino acid side chain, a straight chain or branched $C_1$-$C_6$ alkyl group that may optionally contain a substituted or unsubstituted aryl group, where the carbon atoms of the alkyl and aryl groups each independently comprise hydrogen or fluorine atoms; a straight chain or branched $C_1$-$C_6$ alkyl ether group that may optionally contain a substituted or unsubstituted aryl group where the carbon atoms of the alkyl and aryl groups each independently comprise hydrogen or fluorine atoms; or a straight chain or branched $C_1$-$C_6$ alkoxy group that may optionally contain a substituted or unsubstituted aryl group where the carbon atoms of the alkyl and aryl groups each independently comprise hydrogen or fluorine atoms; where the method (a) covalently tags a biomolecule in the sample with at least one N-substituted piperazine compound or a salt thereof-based chemical affinity tag under conditions to result in a N-substituted piperazine compound or a salt thereof-based chemically tagged biomolecule, (b) selectively captures the N-substituted piperazine compound or a salt thereof-based chemically tagged biomolecule with either (i) a solid support to which an N-substituted piperazine compound epitope or analog thereof-selective antibody is attached, or (ii) a solution comprising an N-substituted piperazine compound epitope or analog thereof-selective antibody, and thereafter contacting the solution with a solid support capable of capturing the N-substituted piperazine compound epitope or analog thereof-selective antibody to selectively capture the N-substituted piperazine compound or a salt thereof-based chemically tagged biomolecule, and (c) elutes the N-substituted piperazine compound or a salt thereof-based chemically tagged biomolecule by adding at least one elution reagent comprising at least one displacement molecule to the solid support to competitively selectively elute under native conditions an intact N-substituted piperazine compound or a salt thereof-based chemically tagged biomolecule.

In one embodiment, the N-substituted piperazine compound or a salt thereof-based chemically affinity tagged biomolecule is a DMPZ-based chemical affinity tag.

In one embodiment, the displacement molecule in step (c) is a substructure of the DMPZ epitope or analog thereof. In one embodiment, the N-substituted piperazine is a bis-trifluoroacetic acid (TFA) salt, a bis-HCl salt, a bis-acetic acid salt, a bis-formic acid salt, and/or a mix of these or other acidic salts.

In embodiments, step (a) is performed on a single sample, or step (a) is performed on at least two separate samples and the separate samples are combined prior to step (b), resulting in a multiplex method.

In one embodiment, the DMPZ-based chemical affinity tag is optionally isotopically labeled. In one embodiment, the DMPZ-based affinity tag has a linking group and a reactive group, where the DMPZ-based chemical affinity tag labels the biomolecule by amine, carboxyl, thiol, carbonyl (aldehyde/ketone), azide, alkyne, cyclic alkyne, and/or phosphine reactive chemistries.

In one embodiment, the elution of step (c) occurs at pH ranging from about 4 to about 10.

In one embodiment, the method further comprises, after step (c), a step (d) where the elution reagent(s) are removed by vacuum drying or desalting with dialysis or reversed phase or size exclusion chromatography. In embodiments, the elution reagents are volatile, and thus are readily removed by, e.g., vacuum drying.

In embodiments, the biomolecule that is tagged is a cell, protein, peptide, glycan, steroid, nucleotide, sugar, toxin, lipid, and/or small metabolite.

In one embodiment, the elution reagent contains at least one displacement molecule. In one embodiment, the displacement molecule(s) is a substructure of the DMPZ epitope and epitope analogs. In one embodiment, the displacement molecule is piperidine, 2-S-methyl piperidine, 2-methyl piperidine, cis-2,6-dimethyl piperidine, 2,2,4,4-tetramethyl piperidine, triethylamine (TEA), and/or diisopropylethylamine. In one embodiment, the displacement molecule is not a substructure of the DMPZ epitope and epitope analogs. In one embodiment, the displacement molecule is triethylamine (TEA), N,N-diisopropylethylamine (DIPEA), triethylammonium acetate (TEAA), and/or triethylammonium bicarbonate (TEAB). In one embodiment, the elution reagent comprises more than one displacement molecule, where the displacement molecules may be a combination of a substructure of the DMPZ epitope and epitope analogs, a combination of compounds which are not a substructure of the DMPZ epitope and epitope analogs, and combinations of substructure of the DMPZ epitope and epitope analogs and compounds which are not a substructure of the DMPZ epitope and epitope analogs. In one embodiment, the elution reagent contains at least one buffer, e.g., Tris, HEPES, TES, phosphate, MES, MOPS, PIPES, bicarbonate, carbonate, tricine, bicine, TEAB, TEAA, etc.

In one embodiment, the DMPZ epitope-selective antibody in step (b) is a glycoform, Fab fragment or derivatives thereof. In addition, the DMPZ epitope to which the described antibody reacts and is present in step (b) of the method comprises a fragment, substructure, structural analog, or a derivative of the DMPZ-based affinity tag.

In embodiments, the DMPZ-based chemical affinity tag added in step (a) has an optional crosslinker.

In one embodiment, the method further comprises after the elution of step (c) or after the removal of elution reagent in step (d), performing mass spectroscopy analysis on the eluted biomolecule.

In embodiments, the solid support of step (b) is a particle, e.g., a magnetic particle, or a plastic, glass, ceramics, silicone, metal, and/or cellulose surface.

In one embodiment, the method may further add at least a second DMPZ-based chemical affinity tag to the sample, different from the first DMPZ-based affinity tag.

In one embodiment, the method further adds at least a second N-substituted piperazine compound or a salt thereof-based chemical affinity tag to the sample, where the second tag is different from the first tag.

In one embodiment of the method, the DMPZ-based chemical affinity tag has the piperazine structure

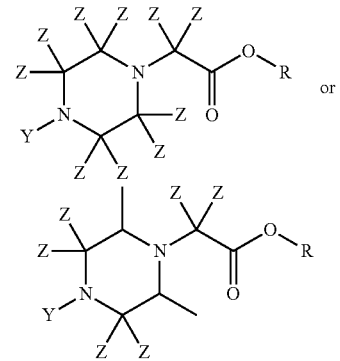

where Y is a straight chain or branched $C_1$-$C_6$ alkyl group or a straight chain or branched $C_1$-$C_6$ alkyl ether group, where the carbon atoms of the alkyl group or alkyl ether group each independently comprise hydrogen, deuterium or fluorine atoms; where R is any length linker comprised of C, N, O, H between the N-substituted ring and the reactive group(s); and where each Z is independently hydrogen, fluorine, chlorine, bromine, iodine, an amino acid side chain, a straight chain or branched $C_1$-$C_6$ alkyl group that may optionally contain a substituted or unsubstituted aryl group wherein the carbon atoms of the alkyl and aryl groups each independently comprise hydrogen or fluorine atoms, a straight chain or branched $C_1$-$C_6$ alkyl ether group that may optionally contain a substituted or unsubstituted aryl group wherein the carbon atoms of the alkyl and aryl groups each independently comprise hydrogen or fluorine atoms, or a straight chain or branched $C_1$-$C_6$ alkoxy group that may optionally contain a substituted or unsubstituted aryl group where the carbon atoms of the alkyl and aryl groups each independently comprise hydrogen or fluorine atoms.

In one embodiment, the displacement molecule in step (c) is sufficiently soluble to permit competitive elution with a concentration 10 to 1,000,000,000 times the affinity binding constant of the DMPZ epitope or analog thereof selective antibody affinity to the DMPZ-based chemical affinity tag. In one embodiment, step (c) is performed at a pH in the range of about 4 to about 10.

In one embodiment, a kit comprises (a) a dimethyl piperidine- (DMP-) based chemical affinity tag, (b) a DMP epitope-selective antibody optionally on a solid support, and (c) a substructure of the DMP epitope and epitope analogs selected from the group consisting of piperidine, 2-S-methyl piperidine, 2-methyl piperidine, 2,2,4,4-tetramethyl piperidine, triethylamine, diisopropylethylamine, and combinations thereof, and (d) instructions for using the kit to selectively label and enrich biomolecules in a sample.

In one embodiment, the kit comprises (a) a dimethyl piperazine- (DMPZ-) chemical affinity tag, (b) a DMPZ epitope-selective antibody optionally on a solid support, and (c) a substructure of a DMPZ epitope or analog thereof, and (d) instructions for using the kit to selectively label and enrich biomolecules in a sample.

In one embodiment, the kit comprises (a) an affinity tag, (b) an anti-affinity tag antibody optionally on a solid support, and (c) a substructure of a dimethyl piperazine or analog thereof, or dimethyl piperidine or analog thereof, and (d) instructions for using the kit to selectively label and enrich biomolecules in a sample.

In embodiments, the affinity tag in the kit is isotopically-labeled. In one embodiment of the kit, the dimethyl piperidine- (DMP-) or dimethyl piperazine- (DMPZ-) based chemical affinity tag is bound or linked to at least one biological entity or a reagent for modification of a biological entity. In one embodiment of the kit, the substructure of the DMP epitope or analogs thereof, or the substructure of a DMPZ epitope or analog thereof, has sufficient solubility to permit competitive elution with a concentration 10 to 1,000,000,000 times the affinity binding constant of the DMP epitope or analog thereof selective antibody, or DMPZ epitope or analog thereof selective antibody affinity to the DMP-based chemical affinity tag or DMPZ-based chemical affinity tag.

In FIG. 1A, antibody is incubated with a sample containing the biomolecule labeled with an epitope tag. A Protein A/G-coated resin is then added to the sample to capture the antibody with its bound antigen. Elution is performed by addition of the small molecule elution reagent and centrifugation to separate the resin from the released analyte in solution. In FIG. 1B, the antibody is coupled directly to the resin, and this resin is incubated with the sample containing the labeled biomolecule. Elution is performed as described above.

Figure 2B:
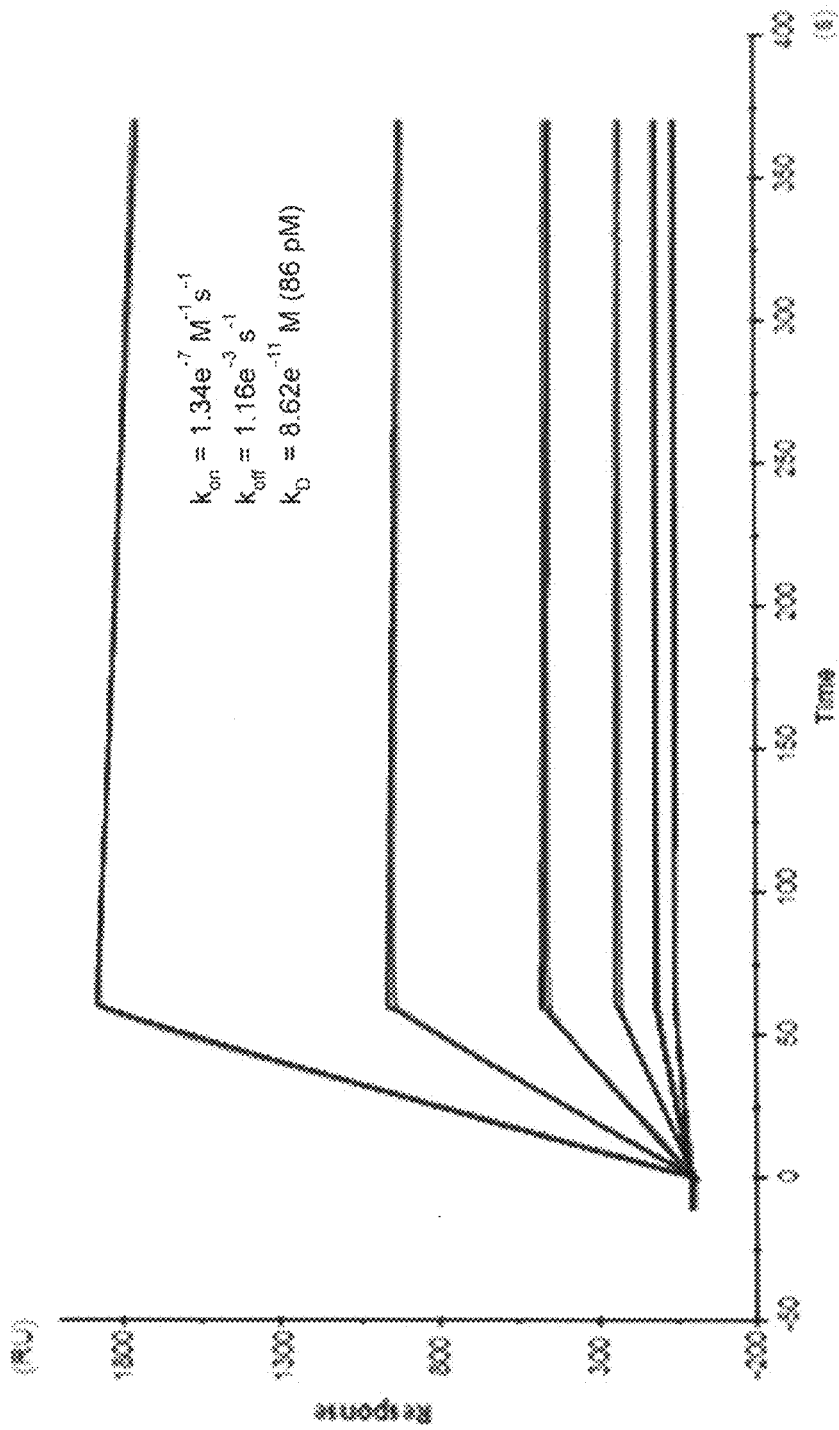
Figure 2C:
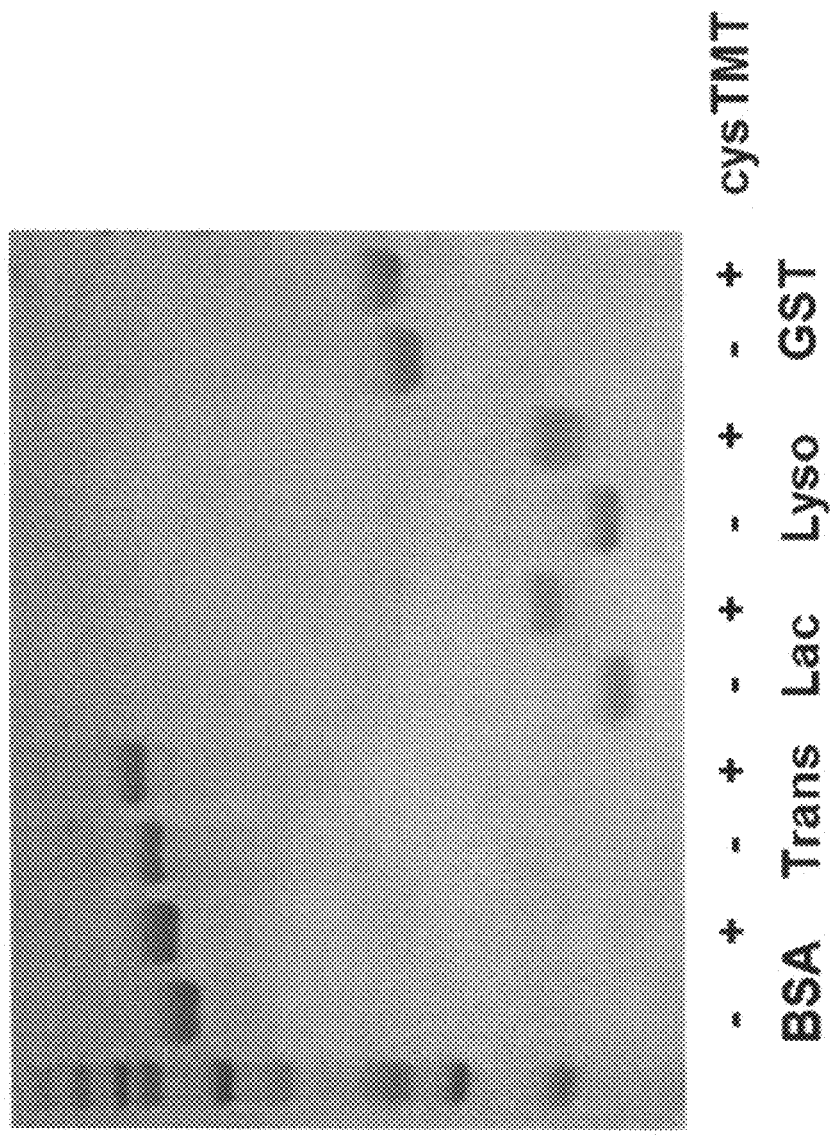

FIG. 2A, B, show surface plasmon resonance of anti-TMT™ hybridomas using a TMT™-labeled surface. FIG. 2C shows SDS-PAGE of unlabeled (−) and cysTMT™-labeled (+) proteins: BSA, transferrin (Trans), lactalbumin (Lac), lysozyme (Lyso) and GST. FIG. 2D shows a Western blot of unlabeled (−) and TMT™-labeled BSA (+) using anti-TMT™ antibody.

Figure 3B:
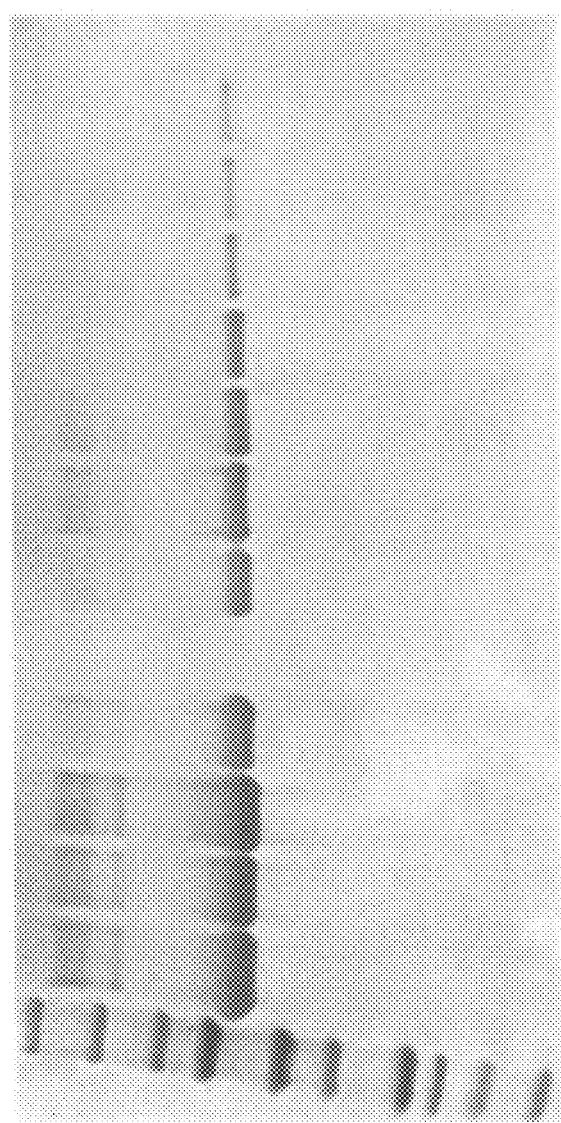

FIG. 3A shows surface plasmon resonance of anti-TMT™ antibody bound to a TMT™ labeled surface exposed to the indicated concentrations of elution reagents dimethyl piperidine (DMP), DMP-aldehyde, and a cysteine-reactive dithiopyridyl-activated DMP (cysTMT™). FIG. 3B shows load (L), flowthrough (FT), and elution of TMT™-labeled bovine serum albumin (BSA) with 50 mM glycine-HCl, pH 2.7 (E) or dimethyl piperidine (DMP) at the indicated concentrations at neutral or high pH.

FIG. 4A shows proteins from an A549 cell lysate that were alkylated on cysteine residues with an iodoacetyl TMT reagent, digested with trypsin, and then captured with anti-TMT immobilized antibody resin. Peptides were washed with Tris buffered saline (TBS), RAPIGEST detergent (Waters), or CHAPS detergent and eluted with 0.4% trifluoracetic acid (pH about 2), or washed with TBS and water prior to elution with DMP at the indicated concentrations and pH. Eluted peptides were analyzed by LC-MS/MS on a Thermo Scientific ORBITRAP XL and data was interpreted with Thermo Scientific PROTEOME DISCOVERER 1.3 to identify the eluted peptides and the number of iodoTMT labeled peptides specifically eluted (percentage shown above each bar). In FIG. 4B, a cell lysate was S-nitrosylated in vitro with nitroglutathione, the free thiols were irreversibly alkylated with iodoacetamide, the nitroso groups were reduced and selectively released with ascorbic acid, the newly exposed cysteines were irreversibly alkylated with iodoTMT, and the samples were then reduced to remove disulfide linkages, alkylated with iodoacetamide, and digested with trypsin. These peptide samples were enriched with the anti-TMT antibody, and samples of the load, the flowthrough, and the non-specific and specific elutions were assessed for peptide recovery and specificity.

Figure 5A:
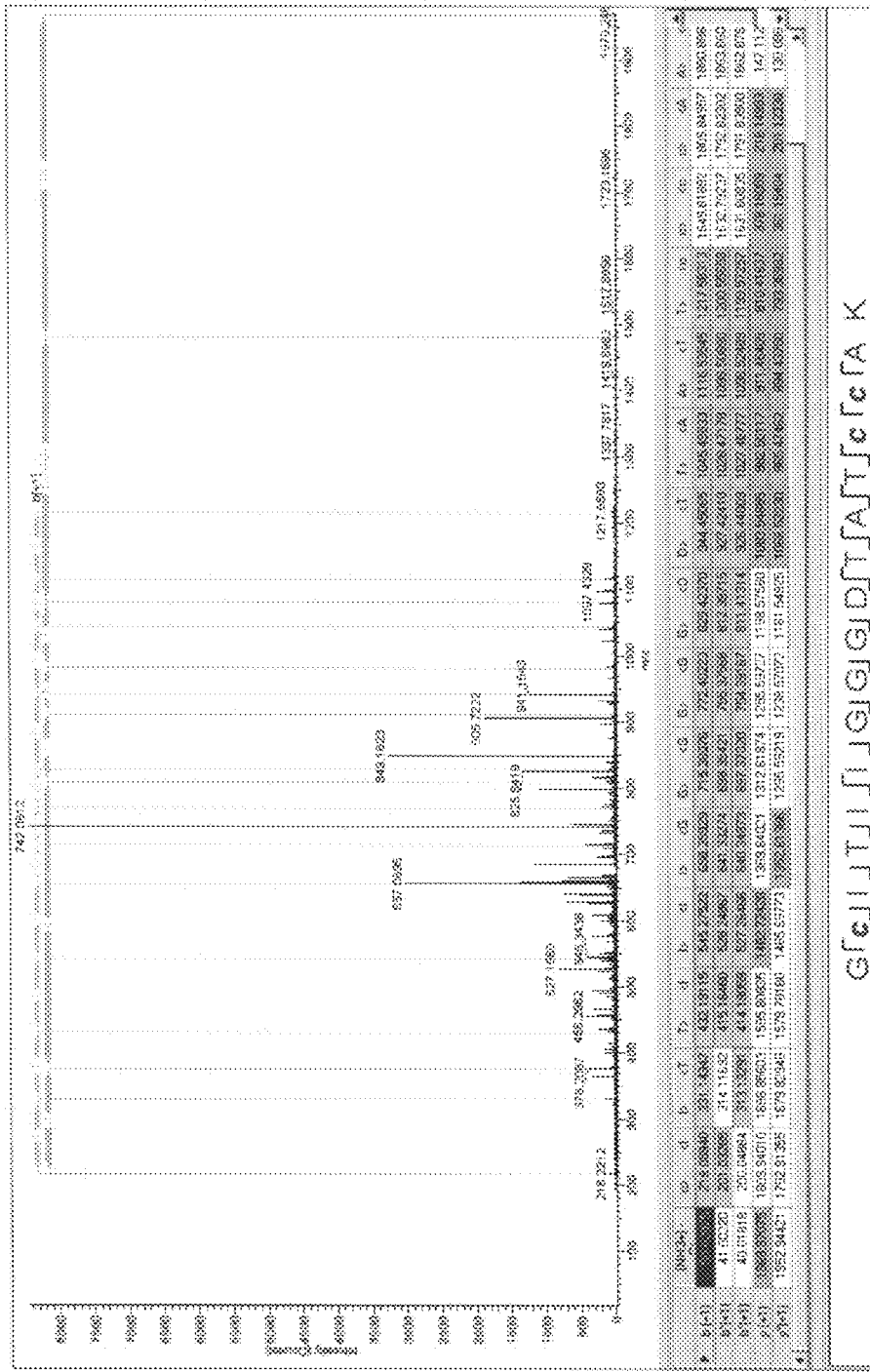
Figure 5B:
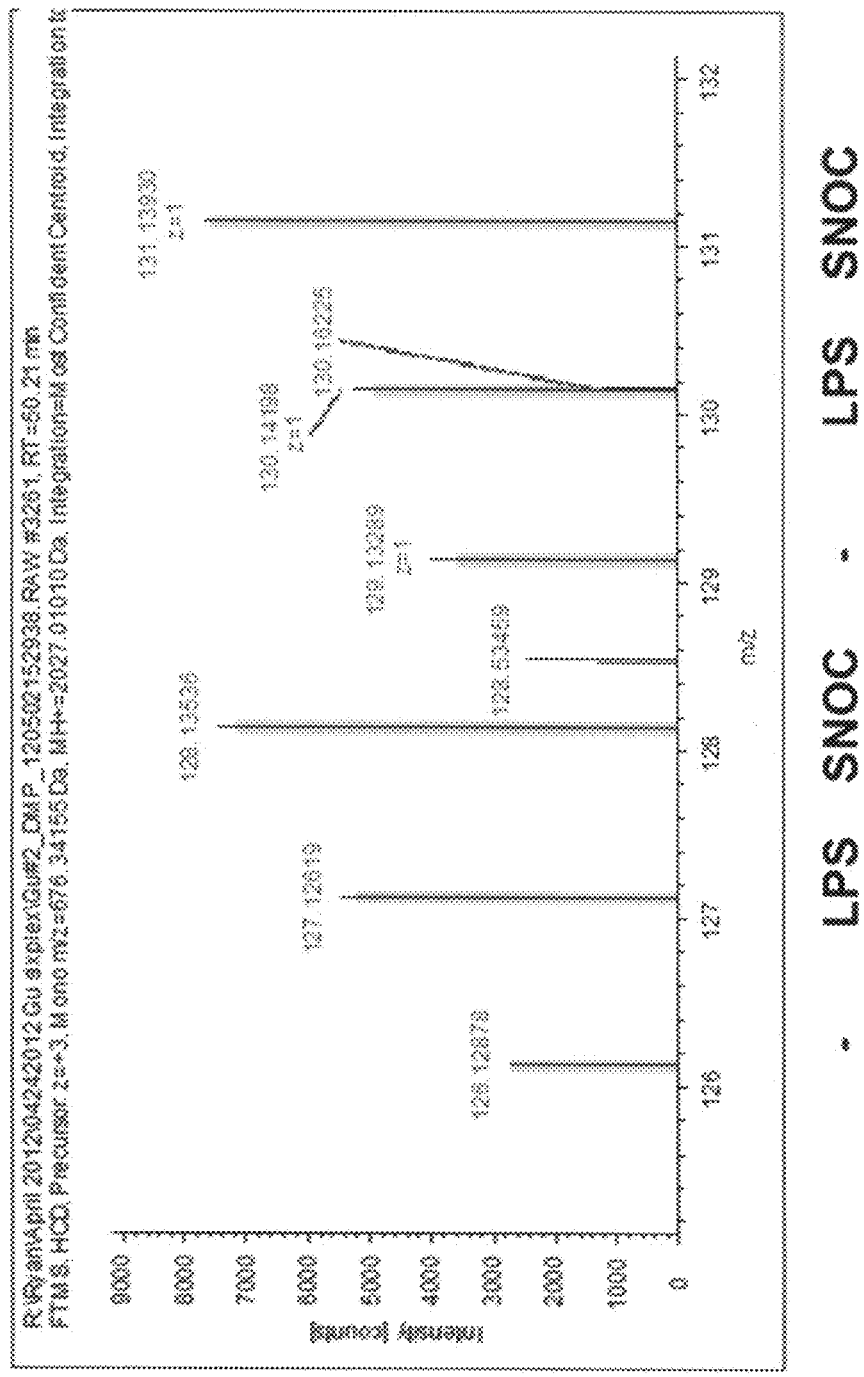

In FIG. 5, showing multiplexed enrichment of S-nitrosylated peptides, cell lysates from a mammalian cell line were treated with vehicle or lipopolysaccharide (LPS) to stimulate S-nitrosylation. A portion of the lysate from untreated cells was also S-nitrosylated in vitro with nitrocysteine (SNOC) as a positive control. As described above, free thiols were alkylated with iodoacetamide, the nitroso groups were selectively released with ascorbic acid, and the newly exposed cysteines were alkylated with an isobaric set of iodoTMT™$^6$ reagents in duplicate. Specifically, the cells treated with vehicle were alkylated with iodoTMT™$^6$-126 and iodoTMT™$^6$-129, the LPS stimulated cells were alkylated with iodoTMT™$^6$-127 and iodoTMT™$^6$-129, and the SNOC treated lysates were alkylated with iodoTMT™$^6$-128 and iodoTMT™$^6$-131. These samples were then reduced, alkylated with iodoacetamide, combined into one tube, and digested with trypsin. These mixed peptide samples were then enriched with the anti-TMT™ antibody in one reaction, and the peptides were identified and quantified by the 126-131 Dalton iodoTMT™ reporter ions. FIG. 5A shows the localization of the site of modification of peptide GCITIIGGGDTATC*CAK (SEQ ID NO:1) from phosphoglycerate kinase 1. The other two cysteines in this peptide were blocked with iodoacetamide, and the site of iodoTMT™ labeling indicates the exact site of S-nitrosylation. FIG. 5B shows quantification of the peptide from FIG. 5A across three conditions in duplicate. FIG. 5C shows quantification of peptide C*MMAQYNR (SEQ ID NO:2) from stress-induced-phosphoprotein 1 (*=site of iodoTMT™ incorporation).

FIG. 6 shows chemical structures of piperidine elution reagents. Multiple variants and structural analogues of piperidine reagents were evaluated for their ability to elute bound TMT™-labeled protein and peptide. The method is also applicable to using a series of isomers or isotopically labeled variants of piperazine-based chemical affinity tags.

Figure 7A:
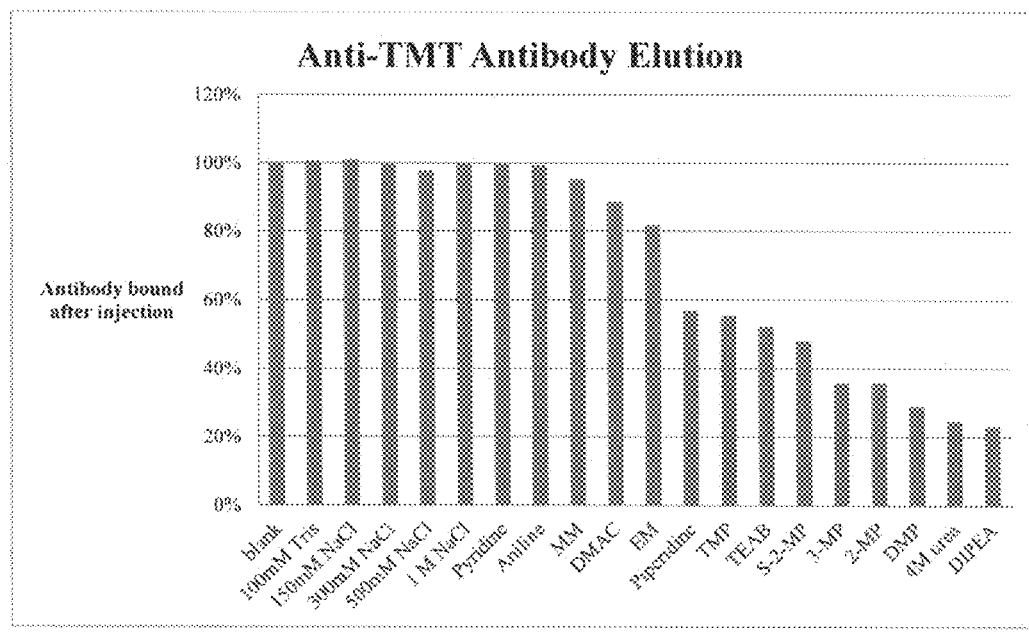

FIG. 7 shows anti-TMT antibody competitive elution using different chemical structures of piperidine and piperazine elution reagents by surface plasmon resonance. FIG. 7A shows percent anti-TMT antibody remaining on a TMT-labeled surface after injection of increasing concentrations of sodium chloride (NaCl) and 100 μM of pyridine, aniline, N-methyl morphorline (MM), N-ethyl morphorline (EM), dimethylacetimide (DMAc), piperidine, cis-2,6-dimethyl piperidine (DMP), 2-S-methyl piperidine (S-2MP), 2-methyl piperidine (2-MP), 2,2,4,4-tetramethyl piperidine (TMP), N,N-diisopropylethylamine (DIPEA), triethylammonium bicarbonate (TEAB) or 4 M urea compared to a blank. FIG. 7B shows percent anti-TMT antibody remaining on a TMT-labeled surface after injection of 1 mM cis-2,6-dimethyl piperidine (DMP), 1,4-dimethyl piperazine (DMPZ), dimethyl glycine (DMG), diethyl glycine (DEG), N,N-diisopropylethylamine (DIPEA), or a buffer containing 500 mM triethylammonium acetate and 10 mM cis-2,6-dimethyl piperidine. In one embodiment, the elution buffer contains 500 mM triethylammonium acetate and 10 mM cis-2,6-dimethyl piperidine. In one embodiment, a TMT elution buffer contains 500 mM triethylammonium acetate and 10 mM cis-2,6-dimethyl piperidine.

FIG. 8 shows chemical structures of isomers and isotopomers. FIG. 8A shows multiple isomers of amine-reactive DMP tags that provide alternative lengths of the linker between the epitope and the reactive groups, with unique benefits of longer linkers for cell or intact protein capture or multiplexed peptide capture and analysis. FIG. 8B shows multiple isotopomers of amine-reactive DMP reagents that provide identical structures but unique isotopic signatures for multiplexed capture and quantitative analysis of tagged samples.

Figure 9:
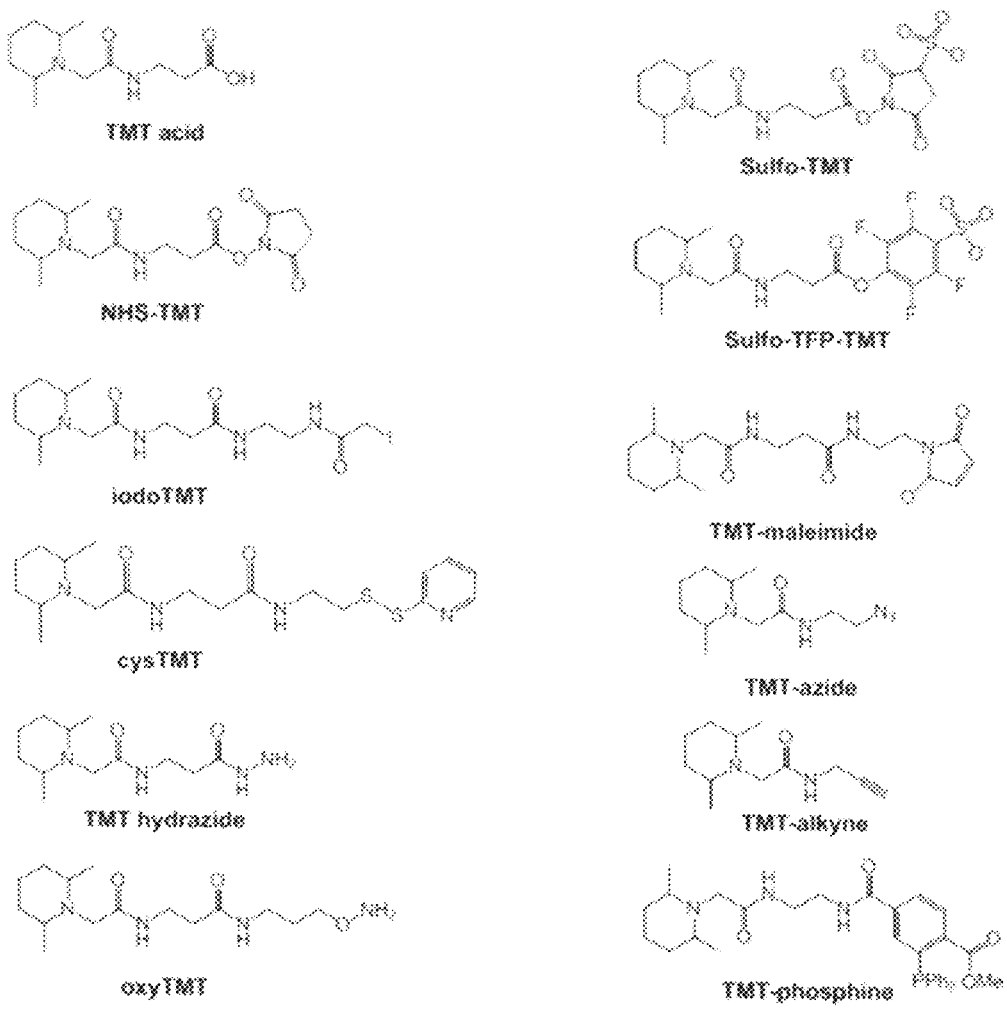
FIG. 9 are chemical structures showing reactivities.

FIG. 9 shows a range of chemical reactivities besides the amine and two cysteine-reactive chemistries described above. All of the reagents contain dimethyl piperidine for the purpose of example, but could also contain other N-substituted piperidine or N-substituted piperazine.

Figure 10:
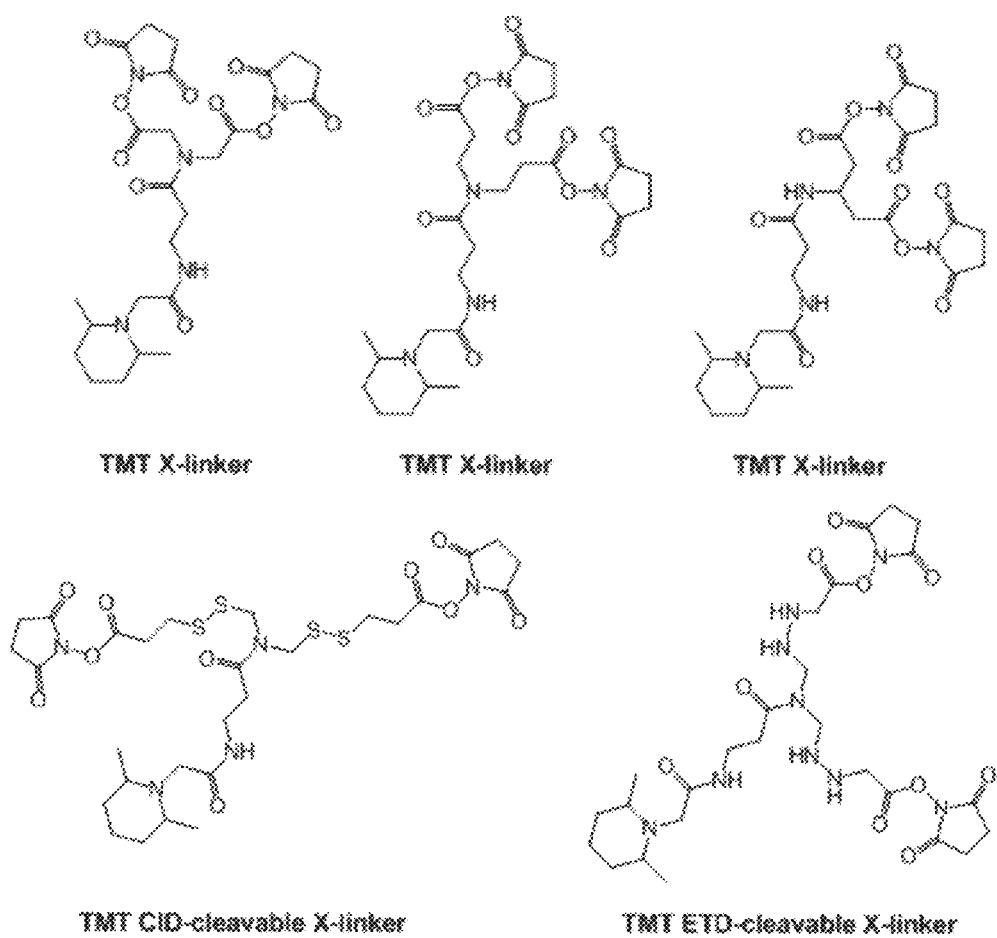
FIG. 10 are chemical structures of crosslinkers.

FIG. 10 shows bifunctional amine-reactive crosslinkers with a DMP tag that allow affinity enrichment of crosslinked proteins and peptides for the molecular characterization of protein interaction sites.

FIG. 11 shows chemical structures for cysteine-reactive tandem mass tags (cysTMT™) labeling in one embodiment. The dithiopyridine chemistry of these tags selectively reacts with thiols of cysteine residues through a reversible disulfide linkage. These tags include a non-isotopically labeled reagent (cysTMTzero™) and six cysTMTsixplex™ reagents with unique distributions of heavy isotopes so that they weigh the same (i.e. are isobaric) but yield unique reporter ions. Biological samples labeled with cysTMTzero™ and any one of the cysTMTsixplex™ reagents can be combined and then selectively captured and analyzed as a duplex pair, with identical peptides from each sample separated by 5 Da. Alternatively, six samples can be labeled with the six isobaric reagents, pooled, and then captured and analyzed as one multiplexed sample.

Figure 12:
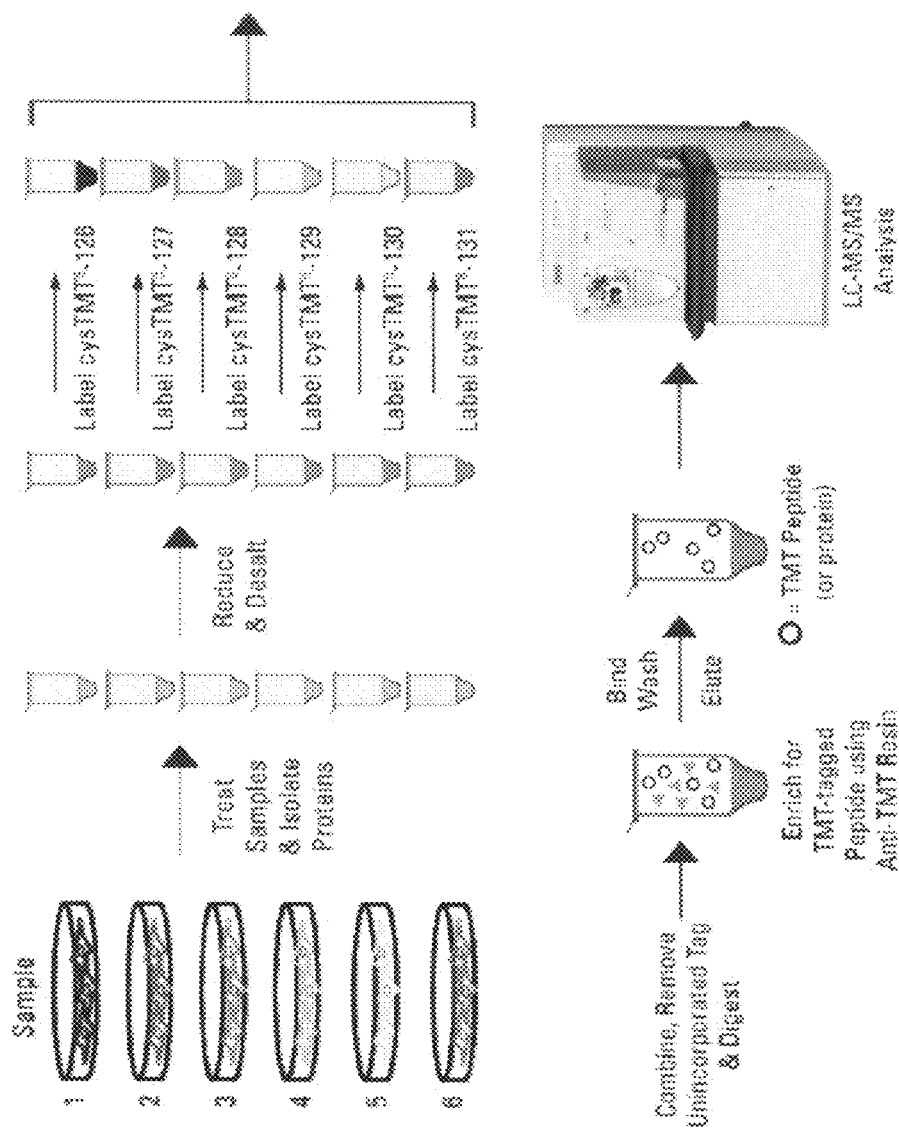
FIG. 12 shows an example work flow for mass spectrometry analysis using cysTMT™ reagents.

FIG. 12 shows an example work flow for mass spectrometry analysis using cysTMT™ reagents in one embodiment. These reagents can be used to label intact proteins from multiple samples before pooling the samples for processing, multiplexed enrichment, and LC-MS/MS analysis.

Figure 13:
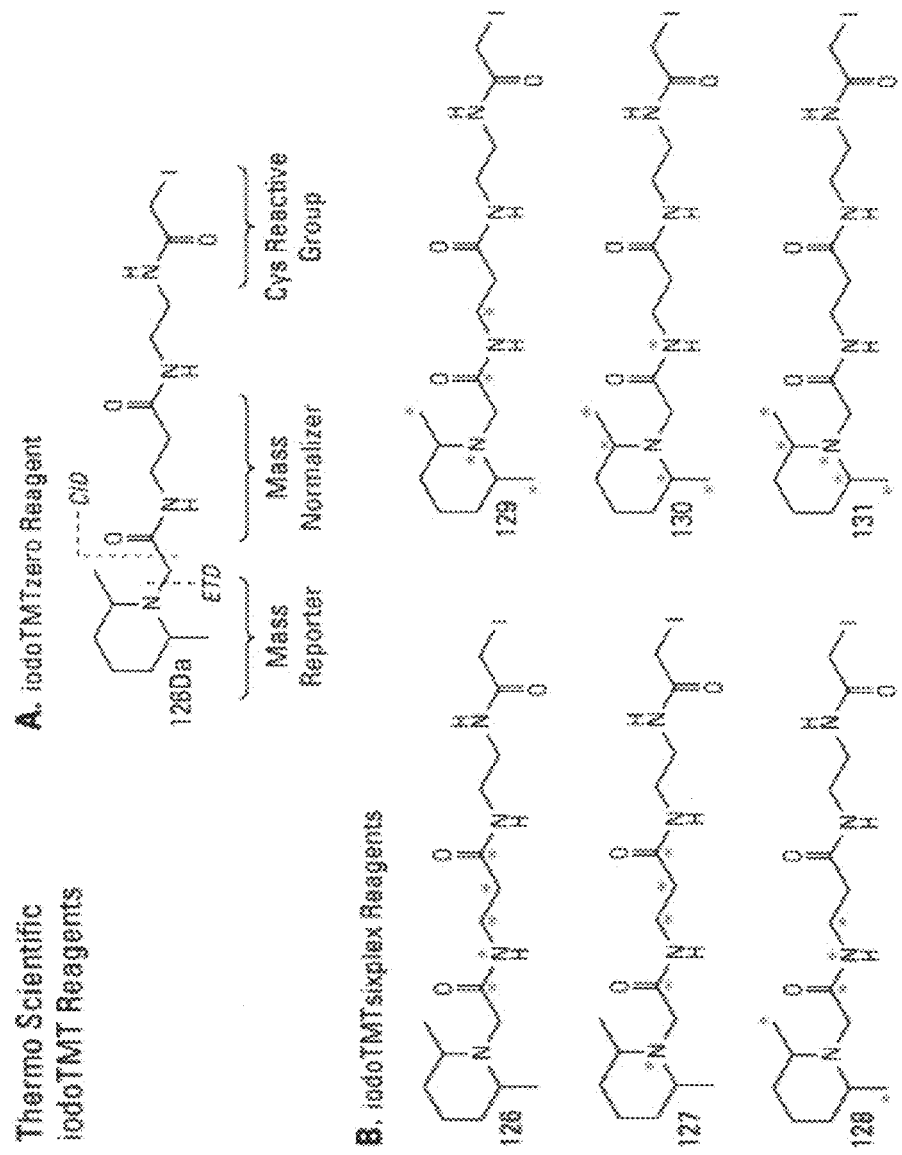
FIG. 13 shows chemical structures for iodoacetyl tandem mass tags (iodoTMT™) labeling.

FIG. 13 shows chemical structures for iodoacetyl tandem mass tags (iodoTMT™) labeling in one embodiment. These tags are analogous to the cysTMT™ reagents, except that the iodoacetyl chemistry is used to label thiols irreversibly.

Figure 14:
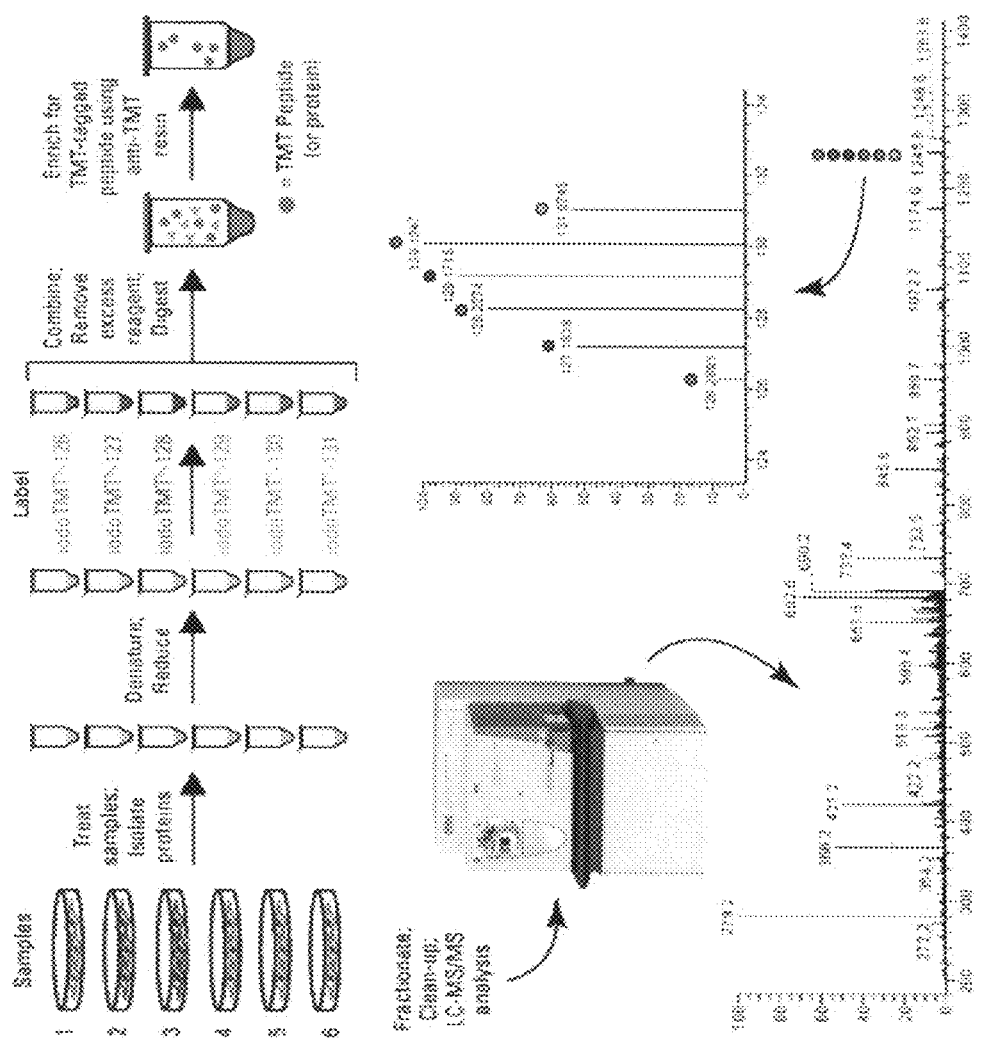
FIG. 14 shows an example work flow for mass spectrometry analysis using iodoTMT™ reagents.

FIG. 14 shows an example work flow for mass spectrometry analysis using iodoTMT™ reagents. The iodoTMT™ reagents are less sensitive to quenching by tris(2-carboxyethyl)phosphine (TCEP), so that the TCEP reducing agent does not need to be removed by dialysis or desalting before labeling with iodoTMT™ chemical tags.

Figure 15A:
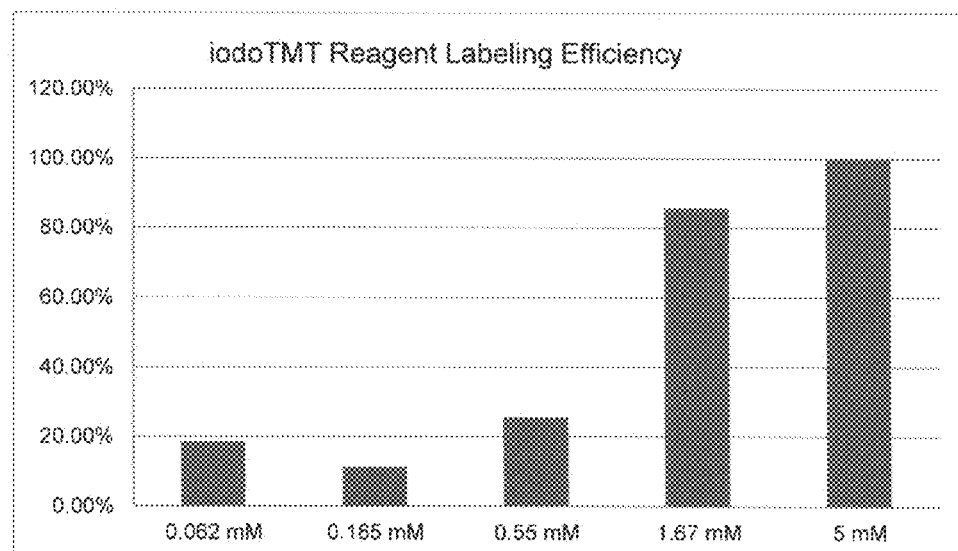
FIGS. 15A-B show iodoTMT™ reagent labeling efficiency and specificity.
Figure 15B:
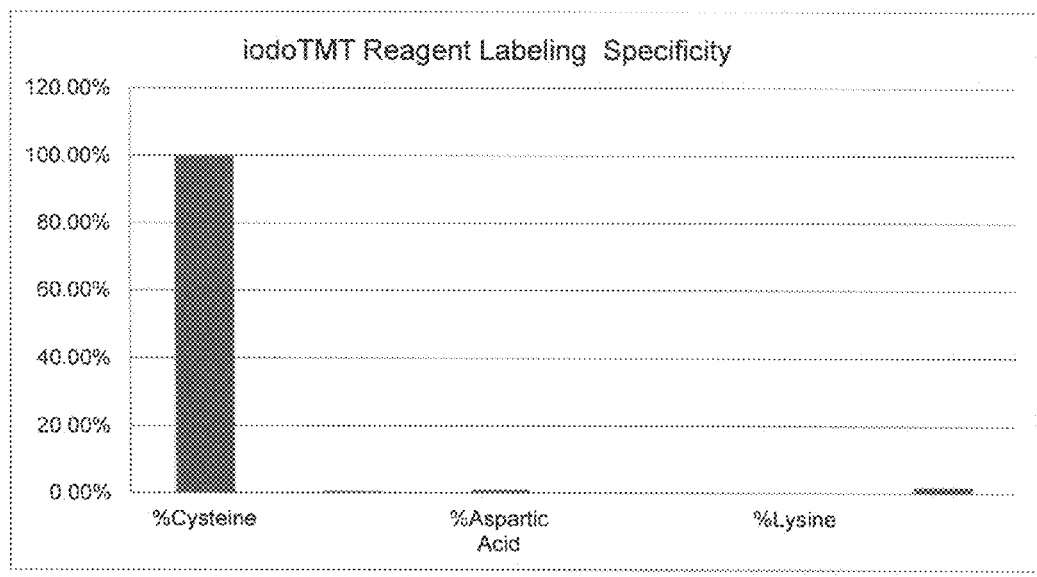

FIGS. 15A-B show iodoTMT™ reagent labeling efficiency and specificity. The iodoTMT™ reagent labeling is sensitive to stoichiometry and pH conditions. Excess reagent or reaction conditions significantly higher or lower than pH 8.0 will result in non-selective labeling at lysines, histidines, aspartates, and glutamate residues.

Figure 16A:
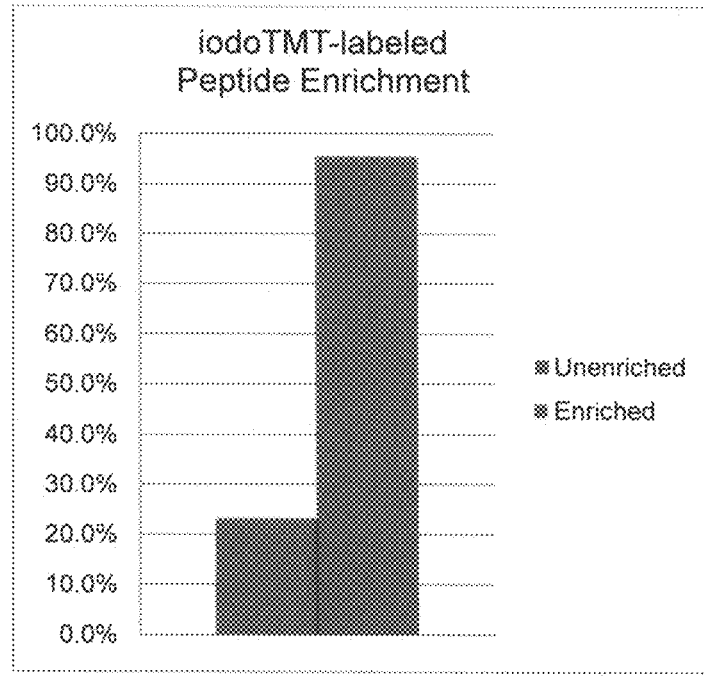
FIGS. 16A-B show iodoTMT™-labeled peptide enrichment and protein identification comparison.
Figure 16B:
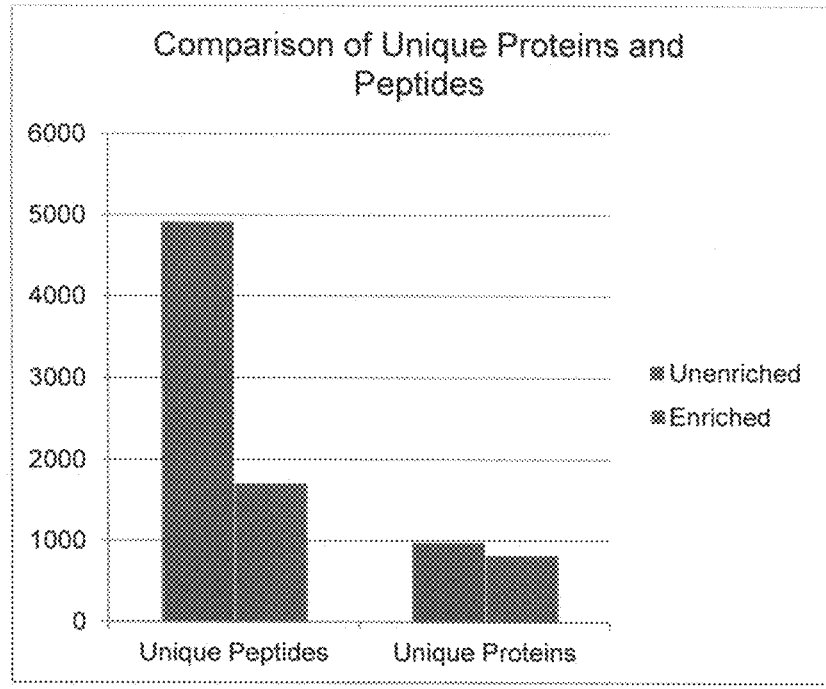

FIGS. 16A-B show iodoTMT™-labeled peptide enrichment and protein identification comparison. While only a subset of peptides contain cysteine residues, the reduction in complexity allowed by selective labeling and enrichment of cysteine-containing peptides results in a greater number of proteins identified from a given number of peptides identified.

Figure 17:
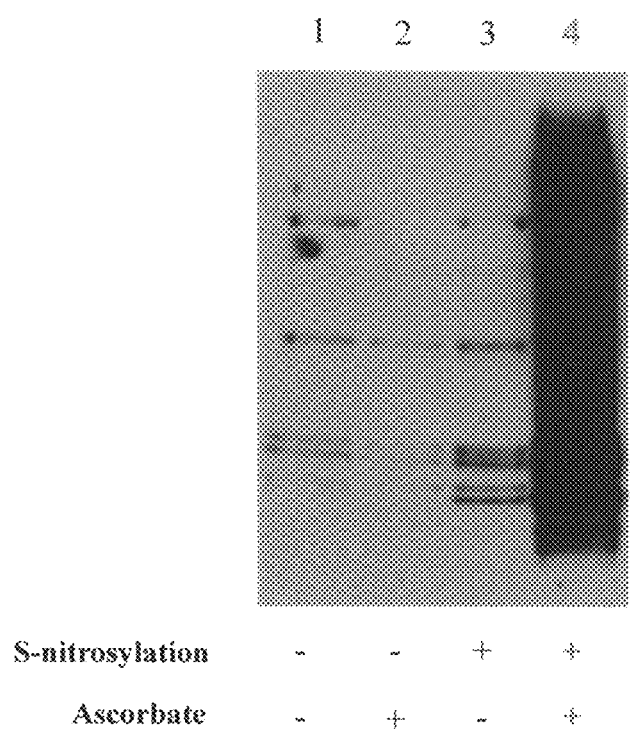
FIG. 17 shows an example of S-nitrosylation Western blotting.

FIG. 17 shows an example of S-nitrosylation Western blotting. A complex cell lysate was treated in vitro with vehicle (lanes 1,2) or nitroglutathione (lanes 3,4) and then free thiols were blocked with iodoacetamide. Nitrosylated thiols can then be labeled with iodoTMT™ after the selective reduction of nitrosylated thiols with ascorbate (lanes 2,4).

Figure 18:
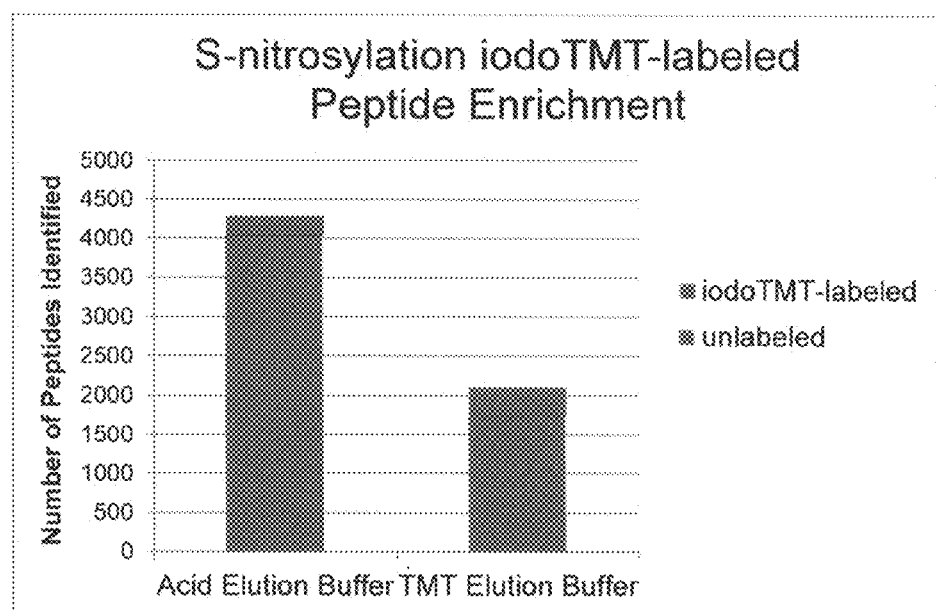
FIG. 18 shows enrichment of S-nitrosylated peptides.

FIG. 18 shows the improved selectivity of enrichment of S-nitrosylated peptides with a soft competitive elution strategy according to one embodiment, instead of acidic elution buffer.

Figure 19:
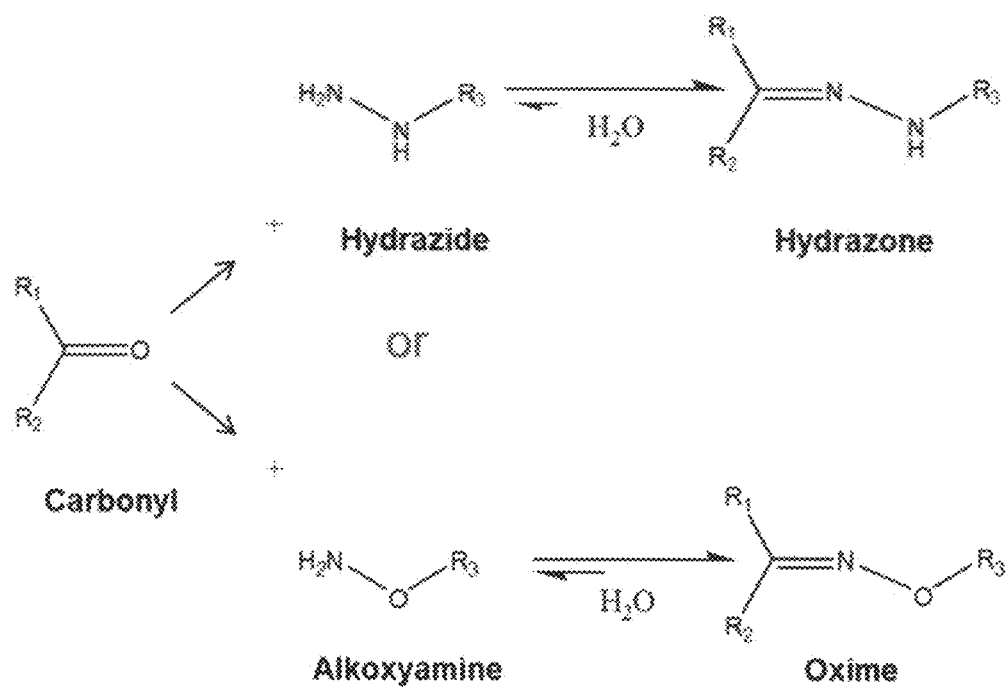
FIG. 19 shows the chemical reaction of aldehydes or ketones with hydrazide or alkoxyamine reagents.

FIG. 19 shows the chemical reactivity of hydrazide and alkoxyamine reagents for the selective labeling, enrichment, identification, and quantification of peptides, glycans, lipids, steroids, nucleotides, and other biomolecules containing aldehydes and ketones.

FIG. 20 show chemical structures for alkoxyamine tandem mass tags (oxyTMT™) labeling in one embodiment.

FIG. 21 shows chemical structures for hydrazide tandem mass tags (hydrazideTMT™) labeling in one embodiment.

Figure 22:
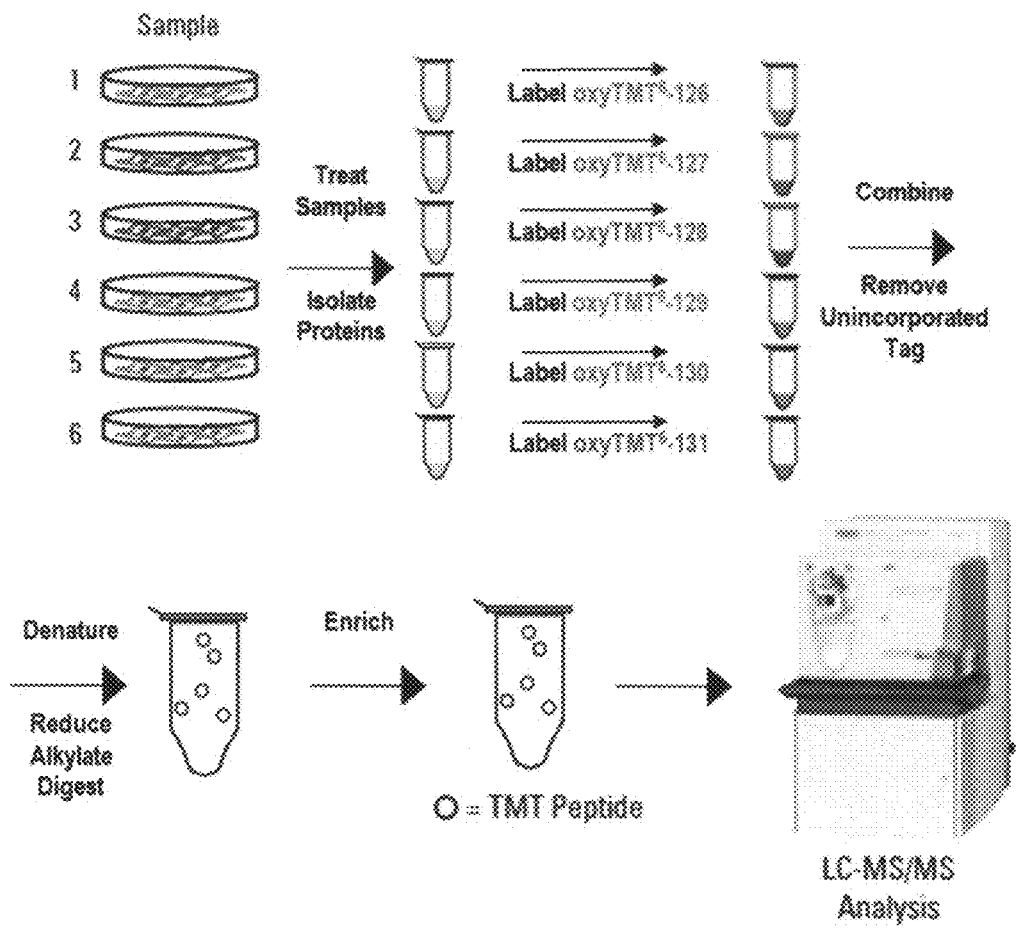
FIG. 22 shows an example work flow for mass spectrometry analysis using oxyTMT™ reagents.

FIG. 22 shows an example work flow for mass spectrometry analysis of proteins using oxyTMT™ reagents.

In one embodiment, the disclosed methods and kits are used to prepare biomolecules for subsequent mass spectrometry (MS) analysis. In one embodiment, the biomolecules are prepared using Thermo Scientific's Tandem Mass Tag reagents (TMT®). For example, the Thermo Scientific Cysteine-Reactive Tandem Mass Tag (cysTMT™) reagents enable selective labeling and relative twoplex to sixplex mass spectrometry (MS) quantitation of cysteine-containing peptides derived from complex biological samples. The cysTMT™ reagents label only free sulfhydryl groups on cysteine residues, in contrast to the amine-reactive TMT® reagents, which in other embodiments, may also be used. To selectively analyze the cysteine-labeled peptides, the sample is enriched using the Thermo Scientific Immobilized Anti-TMT™ Antibody Resin. The cysTMT™ Reagents and Anti-TMT™ Resin are effective for reducing sample complexity, improving dynamic range and studying cysteine modifications. Using this approach of thiol labeling, affinity enrichment and quantitation is similar to isotope-coded affinity tags (ICAT).

Each isobaric cysTMT™ sixplex reagent within a set has the same nominal parent mass and is composed of a sulfhydryl-reactive pyridyldithio group, a MS-neutral spacer arm and an MS/MS reporter (FIG. 11). FIG. 11 shows chemical structure of the Thermo Scientific cysTMT™ Label Reagents. Functional regions of the reagent structure with the isotope positions, MS/MS fragmentation sites and collision-induced reporter ions for each reagent. The molecular weight of the intact cysTMTzero™ reagent is 410.13 Da and the cysTMTsixplex™ is 416.13 Da. The reagents label proteins prepared from up to six biological samples or treatments, which are combined into one sample for the quantitative analysis of relative protein expression. During the MS/MS stage of acquisition to derive fragment ions and sequence information, a unique reporter ion mass also is generated (e.g., 126-131 Da for the cysTMT™6 Isobaric Label Reagents). These reporter ions are in the low mass region of the MS/MS spectrum, providing information on relative protein expression levels.

The cysTMTzero and cysTMTsixplex Reagents are used as isotopic "light" and "heavy" duplex tags for quantitation at the MS stage. These tags enable quantitation of protein expression changes in cell-based and tissue samples that might not be amenable to metabolic isotopic labeling strategies (e.g., SILAC). For example, to label and prepare samples for analysis (FIG. 12), protein extracts are isolated from cultured cells or tissues. After proteins are reduced and desalted, each sample is individually labeled. Excess tag is removed by SDS-PAGE, gel filtration or the Thermo Scientific Pierce Detergent Removal Spin Columns. For LC-MS/MS analysis proteins are digested with a site-specific endoproteinase. After digestion, labeled peptides are enriched using the Immobilized Anti-TMT Antibody Resin and eluted using the disclosed method. Data acquisition is performed on a Thermo Scientific LTQ-ORBITRAP or VELOS-ORBITRAP Mass Spectrometer, and data analysis software is used for protein identification and relative quantitation of the six samples via reporter ions.

EXAMPLE 1

The DMP tags are non-biological detection and capture bioconjugation reagents that serve as strong antigens for antibody development. Multiple hybridomas were developed and identified from mice injected with BSA labeled with an amine-DMP tag (FIG. 2A). These antibodies have binding affinities in the pM to nM range, and can be used for Western blot detection of labeled proteins with little or no interfering background signal (FIG. 2B, D).

EXAMPLE 2

An anti-TMT™ antibody binds tightly to a TMT™-labeled surface, but washing in μM to mM concentrations of DMP and DMP analogs competes for binding and elutes bound antibody within minutes at room temperature (FIG. 3A). Anti-TMT™ antibody resin specifically binds intact protein labeled with amine-reactive TMT® but not unlabeled protein, and the bound protein can be efficiently eluted with micromolar to millimolar dimethyl piperidine. As the protein is labeled at nearly all amine sites, more sites on the protein are likely bound to the resin and more competitor reagent is necessary to elute the bound protein (FIG. 3B).

EXAMPLE 3

Cell lysates were labeled with an irreversible cysteine-reactive iodoacetyl TMT® reagent, digested, and then captured with the anti-TMT™ resin. The bound peptides were eluted non-specifically with different pH and detergent conditions or specifically with different concentrations and pH of DMP elution reagent (FIG. 4A). Non-specific elution conditions resulted in very poor elution efficiency of the alkylated peptides, and the specificity of elution was less than 5%. In contrast, the DMP reagent efficiently eluted over 100 times as many peptides with greater than 90% specificity. Elution with 10 mM DMP was even more efficient with high pH, but the high pH resulted in lower specificity of elution. As DMP is not a biological molecule, there is no interference from endogenous levels. In contrast, biotinylated molecules are more difficult to recover and may result in the enrichment of interfering endogenously biotinylated molecules.

EXAMPLE 4

The cysteine-reactive DMP tags and affinity enrichment reagents are used for the enrichment, detection, and quantification of low abundance protein modifications. A cell lysate was S-nitrosylated in vitro with nitroglutathione, remaining free thiols were alkylated with iodoacetamide, the nitroso groups were selectively released with ascorbic acid, the newly exposed cysteines were alkylated with iodoTMT™, and the samples were then reduced, alkylated with iodoacetamide, and digested with trypsin. These peptide samples were then enriched with the anti-TMT™ antibody, and a sample of the load, the flowthrough, and the non-specific and specific elutions were assessed for peptide recovery and specificity (FIG. 4B). Even after in vitro labeling as a positive control, this modification is undetectable without enrichment. The specific elution with DMP yielded approximately 50% more peptides than a low pH elution, and the specificity of the enrichment of iodoTMT™-labeled peptides increased from 6% to 21% with specific elution.

EXAMPLE 5

Multiplexed enrichment of low abundance protein modifications is essential for the elucidation of mechanisms, pathways, and downstream effects of biological signaling. Low abundance modifications are difficult to detect and quantify, and multiplexed quantitative methods that reduce variability introduced during sample handling are beneficial. The combined use of isobaric versions of a cysteine-reactive DMP reagent with multiplexed enrichment, efficient elution, and multiplexed quantification allowed the analysis of replicates from multiple experiment conditions, such as the enrichment of S-nitrosylated peptides from in vivo and in vitro stimulated cells. S-nitrosylated peptides from more than 80 proteins were identified and quantified across conditions, and many of these peptides appeared to be regulated by both in vivo treatment of cells with lipopolysaccharide and by in vitro S-nitrosylation with nitrocysteine (FIG. 5).

EXAMPLE 6

Shorter linkers are beneficial for peptide capture and identification, while longer linkers are beneficial for intact protein or cell capture. Successful dentification of peptides by mass spectrometry is affected by the molecular weight of covalently attached tags, such that longer tags result in lower identification rates (Pichler, 2010). In contrast, longer chain linkers connecting the reactive and epitope regions of the tag may provide greater accessibility for buried sites. For example, a chemical probe that covalently labels the catalytic active site of an enzyme may have greater reaction rates and/or capture efficiency for the intact protein when a longer polyethylene glycol spacer separates the reactive and epitope ends of the probe because of the improved accessibility of the reactive end to the reaction site and/or greater accessibility of the epitope after labeling (Kidd 2001).

EXAMPLE 7

Labeling of oxidized proteins with hydrazide and alkoxy reagents, digestion, capture, and quantitation to identify sites prone to oxidative damage under multiple conditions. The ability to identify proteins and protein sites prone to oxidative damage, such as carbonylation, is important for the study of aging and degenerative disease states, and to characterize biologically active therapeutics, including therapeutic antibodies and bioactive protein-based hormones. For example, proteins prone to oxidative damage may provide important insights into the mechanisms of aging and disease, and multiple proteins have been identified that are oxidatively damaged during aging (Feng 2008). The ability to identify and quantify the specific sites of oxidative damage with efficient and specific capture and recovery of modified and labeled peptides provides detailed insights into the mechanisms of aging and toxicity. The structural mapping of proteins and protein interactions can be studied by mapping sites accessible to protein oxidation in the presence of multiple partners and conditions including concentration dependence and time-courses (Xu 2007). These sites of oxidation are labeled with a set of affinity tags, the samples are mixed digested, and labeled peptides are enriched and quantified to provide insights into protein conformation and interactions.

EXAMPLE 8

Cell surface labeling with S-NHS or S-TFP versions of these affinity tags are used for identification and quantification of cell surface proteins that are differentially present on the surface in response to treatment conditions, such as drug, toxin, hormone, differentiating conditions, or environmental stressors (e.g. pH, osmolarity, temperature, $pO_2$). Cultured cells are treated with control and one or more treatment conditions, including time-course and dose-response, and then multiple isomers or analogs of the S-NHS or S-TFP reagents are used to label cell surface proteins (FIG. 9). The samples are then mixed before or after lysis and solubilization, and then labeled proteins are enriched, reduced and alkylated to break disulfide bonds, digested with a protease such as trypsin, and then quantitatively analyzed by mass spectrometry to identify cell surface proteins that change in response to treatment or differentiation.

EXAMPLE 9

Bioorthogonal labeling is a strategy that introduces non-native chemical functionality into naturally occurring biomolecules of a living system. This includes labeling with non-native derivatives of amino acids, sugars, lipids, and precursor molecules with azide, alkyne, cyclic alkyne, or phosphine functional groups (FIG. 8). In one example, cells are grown in the presence of azido-sugars, including N-azido acetylgalactosamine, N-azido acetylglucosamine, or N-azido acetylmannosamine. These sugars are incorporated into the complex glycans of glycosylated proteins. Cells treated with multiple conditions, such as drug, toxin, hormone, differentiating conditions, or environmental stressors, and then labeled via the azide-sugars with a set of isomers or analogs of the phosphine or alkyne reagents. These samples are combined and the glycosylated proteins are enriched in one capture experiment with the affinity tag, antibody, and soft elution competitor. These enriched proteins are then reduced, alkylated, and digested prior to identification and quantification by mass spectrometry.

EXAMPLE 10

The disclosed gentle release reagents allow sensitive biomolecules, including intact proteins and cells, to be enriched and purified without damage from harsh elution conditions. An antibody specific for a cell surface marker is labeled with an affinity tag, and then this antibody is incubated with a suspended mixture of cells, such as from a blood sample. An antibody specific for the affinity tag is immobilized on magnetic particles, and these particles are incubated with the sample to enrich cells expressing the specific antigen. After cell enrichment, the immobilized antibody-affinity tag interaction is competitively displaced with the DMP elution reagent(s) under otherwise native, non-destructive conditions. The purified cells are then cultured and expanded for further study.

EXAMPLE 11

Studies of transient or weak protein interactions often utilize protein crosslinkers to stabilize the interactions, to provide molecular detail of the regions or positions of interaction, and to provide distance information by using crosslinkers of various lengths. These crosslinked peptides are relatively rare because of the low labeling efficiency and the complexity of the labeled samples, so various strategies have been developed to improve the analysis. Isotopically paired crosslinkers differing only in the number of heavy stable isotopes in their chemical composition is a powerful identifier of low abundant peptides, as singly crosslinked peptides will appear as distinct doublets in the mass spectrometer (Muller 2001). Trifunctional crosslinkers with affinity tags have also been utilized to allow enrichment of crosslinked peptides from the complex background (Tang 2009). Isotopically labeled trifunctional crosslinkers that consist of two reactive groups and the affinity tag are presented in which the reactive groups are separated by different chain lengths and one or more bonds that are more labile bonds, such as disulfide or hydrazone bonds (FIG. 10). In this example, isotopically labeled trifunctional crosslinkers with the soft elution tag are used to crosslink proteins in multiple conditions (e.g. interaction partner concentration, crosslinker concentration, time course, etc.). The samples are pooled, reduced, alkylated, and digested, and then crosslinked peptides from multiple treatments are simultaneously enriched for analysis. The presence of selectively labile positions in the crosslinker allows enriched, crosslinked peptides to be selectively fragmented at these positions in a trap-based mass spectrometer capable of MS3 fragmentation, and the resulting fragments can be re-isolated for subsequent higher energy fragmentation for peptide sequence assignment (Gardner 2010, Wu 2009). In this manner, the positions of chemical crosslinking can be identified, optimized, and verified under multiple conditions concurrently.

EXAMPLE 12

Improved specific enrichment and competitive elution of S-nitrosylated peptides labeled with multiplex, iodoacetyl tandem mass tag (iodoTMT™) reagents was obtained using an anti-TMT™ antibody resin and competitive TMT® elution buffer. Tandem Mass Tag® (TMT®) reagents (Thermo Scientific) enabled concurrent identification and multiplexed quantitation of proteins in different samples using tandem mass spectrometry (MS).

An isobaric, cysteine-reactive TMT® reagent containing an iodoacetyl-reactive group (iodoTMT™) was previously used for irreversible labeling cysteine-containing peptides (FIG. 13). FIG. 13 shows chemical structures for iodoacetyl tandem mass tags (iodoTMT™) labeling in one embodiment. These tags are analogous to the cysTMT™ reagents, except that the iodoacetyl chemistry is used to label thiols irreversibly. Because cysteine-containing peptides in proteomic samples are present in relatively low abundance, selective enrichment of labeled peptides was required for quantification. When iodoTMT™ was used to label different cysteine-modified peptide subpopulations, there was an even greater challenge in sample enrichment selectivity.

For iodoTMT™-labeled peptides, an anti-TMT™ antibody resin is used for peptide capture with a novel TMT® elution buffer using small molecule analogs of the TMT® reagent reporter region. The inventive reagent provided selective, competitive elution of iodoTMT™-labeled peptides (FIG. 14). FIG. 14 shows an example work flow for mass spectrometry analysis using iodoTMT™ reagents. The iodoTMT™ reagents are less sensitive to quenching by tris(2-carboxyethyl)phosphine (TCEP), so that the TCEP reducing agent does not need to be removed by dialysis or desalting before labeling with iodoTMT™ chemical tags.

For total cysteine alkylation, cell lysates and purified proteins were denatured, reduced, and labeled with excess iodoTMTzero or iodoTMTsixplex reagents prior to enzymatic digestion. For cysteine S-nitrosylation quantitation, samples were treated with nitrosylation donor agents (e.g. GSH-NO) and alkylated with methyl methanethiosulfonate (MMTS) to block unmodified sulfhydryl groups. After desalting, S-nitrosyl groups were selectively reduced using ascorbate to generate free sulfhydryl groups for iodoTMT reagent labeling. An anti-TMT antibody resin was used for labeled peptide enrichment. Peptide samples were analyzed using a Thermo Scientific LTQ™ ORBITRAP XL mass spectrometer. Data were analyzed using Thermo Scientific PROTEOME DISCOVERER 1.3 software. Elution buffer was evaluated by surface plasmon resonance (SPR) using a TMT-derivatized CM5 chip on a GE Healthcare BIACORE 3000 instrument.

The inventive iodoTMT™ reagent labeling was specific and efficient for cysteine sulfhydryl residues with reactivity similar to iodoacetamide (FIG. 15). FIGS. 15A-B show iodoTMT™ reagent labeling efficiency and specificity. The iodoTMT™ reagent labeling is sensitive to stoichiometry and pH conditions. Excess reagent or reaction conditions significantly higher or lower than pH 8.0 will result in non-selective labeling at lysines, histidines, aspartates, and glutamate residues. Because iodoTMT™ reagent labeling was covalent and irreversible, reducing agents did not need to be removed from protein samples before labeling. IodoTMT™ reagents were also used for quantifying cysteine modifications such as S-nitrosylation, oxidation, and di-sulfide bridges.

The enrichment workflow permitted cysteine-containing peptide mutiplex quantitation by LC-MS. Enrichment of iodoTMT™-labeled peptides was facilitated using an anti-TMT™ antibody raised against the reporter region of the TMT® reagents. Elution buffers with low pH or containing denaturants (e.g. urea or SDS) that disrupt antibody-antigen interactions are sometimes used for peptide elution; they also elute any non-specific, unlabeled peptides bound to the resin.

To improve iodoTMT™-labeled peptide elution specificity, various small molecule analogs of the TMT® reagent reporter region as potential compounds for competitive elution were investigated. Using these analogs, structural features of the anti-TMT™ antibody recognition site were identified by SPR using a TMT™-derivatized Biacore chip. The relative affinity of each analog was also determined for the anti-TMT™ binding by competitive elution. The inventive TMT® elution buffer resulted in increased labeled peptide enrichment specificity from 80% to 96% using total cysteine-labeled peptide samples (FIG. 16). FIGS. 16A-B show iodoTMT™-labeled peptide enrichment and protein identification comparison. While only a subset of peptides contain cysteine residues, the reduction in complexity allowed by selective labeling and enrichment of cysteine-containing peptides results in a greater number of proteins identified from a given number of peptides identified.

IodoTMT™ reagents were also used as a probe for labeling S-nitrosylated cysteines in a modified S-nitro switch assay. IodoTMT™ reagents successfully labeled S-nitrosylated cysteines after selective reduction using ascorbate, shown by an anti-TMT™ antibody Western blot (FIG. 17). FIG. 17 shows an example of S-nitrosylation Western blotting. A complex cell lysate was treated in vitro with vehicle (lanes 1,2) or nitroglutathione (lanes 3,4) and then free thiols were blocked with iodoacetamide. Nitrosylated thiols can then be labeled with iodoTMT™ after the selective reduction of nitrosylated thiols with ascorbate (lanes 2,4). Enrichment specificity using low pH and TMT® analog elution buffers for S-nitrosylated samples also resulted; there was a 50% increase in iodoTMT™-labeled peptide identification by LC-MS using the inventive TMT® elution buffer (FIG. 18) which shows improved selectivity of enrichment of S-nitrosylated peptides with a soft competitive elution strategy instead of acidic elution buffer.

EXAMPLE 13

Differential human serum analysis is performed using multiplex iodoTMT™ reagents. Serum protein cysteines are labeled with irreversible, multiplex isobaric mass tags enriched using an anti-isobaric tag antibody for LC-MS analysis.

Iodoacetyl TANDEM MASS TAG (iodoTMT™) reagents (Thermo Scientific) enable concurrent identification and multiplexed quantitation of cysteine-containing proteins using tandem mass spectrometry (MS).

Similar to amine-reactive TMT® reagents, iodoTMT™ reagents are a set of six isobaric mass tags used to label different samples that are combined for a relative quantitation of peptides in a single MS analysis. Differential analysis of human serum by MS is challenging due to high concentrations of albumin and IgG. Removal of these proteins using various depletion strategies is often essential to study low-abundant proteins. Serum sample preparation MS workflow consisted of antibody-based Top 12 abundant protein depletion, iodoTMT™ reagent labeling/enrichment, and LC-MS analysis.

Human serum (10 μL-20 μL) from normal or disease models is processed using Thermo Scientific PIERCE TOP 12 ABUNDANT PROTEIN DEPLETION SPIN COLUMNS, AGILENT HUMAN 14 MULTIPLE AFFINITY REMOVAL SPIN CARTRIDGES, or SIGMA SEPPRO* IgY14 spin columns according to manufacturer's protocols.

Total protein in the depleted fractions is determined using BCA protein assay. For cysteine protein analysis, depleted serum samples are denatured, reduced, and labeled with excess iodoTMTsixplex reagents prior to enzymatic digestion. An anti-TMT antibody resin is used for labeled peptide enrichment, and the inventive TMT Elution Buffer is used for iodoTMT-labeled peptide elution. Peptide samples are analyzed using a Thermo Scientific LTQ™ ORBITRAP XL mass spectrometer. Data are analyzed with Thermo Scientific PROTEOME DISCOVERER 1.4 software.

A serum sample MS workflow combined top 12 abundant protein depletion with iodoTMT™ reagent labeling and enrichment. This workflow is similar to previously published workflows using ICAT reagents but enables sixplex relative quantitation using LC-MS/MS. Three different antibody-based depletion resins for serum sample preparation are compared. The Pierce Top 12 Abundant Protein Depletion Spin Columns provides equivalent depletion of abundant serum proteins but in a more convenient single use format at a significant lower cost per sample.

Depleted serum samples are also labeled using iodoTMT™ reagents to determine differences in relative protein abundance between normal and disease samples. Analysis of iodoTMT™-labeled samples before and after enrichment with anti-TMT™ antibody resin show increased quantifiable peptides, from <30% before enrichment to >90% after enrichment. The high specificity of iodoTMT™-labeled peptide enrichment is further enhanced using a competitive anti-TMT™ antibody elution buffer. By combining abundant serum protein depletion with iodoTMT™ reagent-based quantitation, identification and quantitation of lower abundance serum proteins are significantly improved.

EXAMPLE 14

Labeling of oxidized proteins with hydrazide and alkoxy reagents, digestion, capture, and quantitation identified sites prone to oxidative damage under multiple conditions. Protein oxidative damage results in carbonylation and incorporation of reactive aldehyde and ketone groups into amino acid side chains (Xu 2007). This oxidative damage can occur in vivo in response to environmental stresses, resulting in permanent damage to proteins. The ability to identify proteins and protein sites prone to oxidative damage, such as carbonylation, is important for the study of aging and degenerative disease states, and for characterizing biologically active therapeutics including therapeutic antibodies and bioactive protein-based hormones. For example, proteins prone to oxidative damage may provide important insights into the mechanisms of aging and disease, and multiple proteins have been identified that are oxidatively damaged during aging (Feng 2008). Protein oxidation may be induced in vitro accidentally during preparation or intentionally with heavy metal-catalyzed production of free radicals, by ionizing radiation, or by the addition of peroxides or other free radical producing chemicals to modify proteins at accessible sites for protein structural mapping and protein interaction studies. These modifications may be selectively labeled with alkoxyamine or hydrazide reagents (FIG. 19). FIG. 19 shows the chemical reactivity of hydrazide and alkoxyamine reagents for the selective labeling, enrichment, identification, and quantification of peptides, glycans, lipids, steroids, nucleotides, and other biomolecules containing aldehydes and ketones. Sets of chemical tags containing alkoxyamine or hydrazide groups can be used in a multiplexed fashion to label samples produced from different treatment conditions or time-courses (FIGS. 20, 21). These samples can be labeled under denaturing conditions, mixed, processed, enriched, and analyzed as one sample by LC-MS/MS (FIG. 22). FIG. 22 shows an example work flow for mass spectrometry analysis of proteins using oxyTMT™ reagents. This workflow allows the exact sites of modification to be identified and simultaneously quantified across the experimental conditions to provide insights into disease, sample preparation and manufacturing processes, protein conformation, and interactions.

A method for profiling carbonylated peptides used a novel TMT® capable of determining sites of modification and multiplexed quantification. Protein carbonylation is a common post-translational modification that is linked to many diseases. Technologies for protein carbonylation fall short because they do not allow multiplexed quantitative comparisons, and are limited for determining site and type of modifications. Isobaric Tandem Mass Tags (TMT®) reagents (Thermo Fisher) offer advantages to quantitative proteomics, distinctly multiplexed quantification, and sequence identification. TMT® consists of a reactive group for covalent labeling of proteins or peptides, a reporter group for relative quantification after peptide fragmentation (mass between 126 and 131 Daltons), and a cleavable linker to keep the overall mass constant (isobaric). A novel aldehyde-reactive tandem mass tag, oxyTMT™, was used for labeling based on an aminoxy functional group using tandem mass spectrometry.

Carbonylated proteins were prepared using bovine serum albumin (BSA) as standard protein and mouse liver mitochondria as complex lysate reduced with TCEP; these were labeled with 4-hydroxynonenol (HNE) which is widely used in the study of oxidative damage because it modifies cysteines, lysines, and histidines. A liver mitochondria sample was not labeled with HNE as an endogenous carbonylated sample. After assessing labeling conditions, proteins were labeled with 10 mM TMT reagent in MES buffer, pH 5. Labeled proteins were alkylated with iodoacetamide and enzymatically digested with trypsin. Labeled peptides were passed through anti-TMT resin, eluted with elution buffer and desalted by C18 Stage Tip. Peptides were analyzed by LC-MS/MS using ESI LTQ ORBITRAP VELOS mass spectrometry. All data were searched by PROTEINPILOT program (version 4.5 AB SCIEX) against a mouse database containing BSA sequence.

Initial optimization was performed with analysis of standard, single protein BSA, with carbonyl modifications introduced by HNE modification by in vitro incubation with excess HNE, an aldehyde-containing lipid metabolic compound, in physiological PBS buffer. Carbonyl modification of BSA was confirmed by gel electrophoresis and Western blot using anti-HNE antibody. Modified BSA was incubated with excess TMT reagent, dialyzed, and digested with trypsin, and the TMT labeled carbonylated peptides enriched using anti-TMT resin followed by LC-MS/MS analysis by ESI LTQ ORBITRAP VELOS mass spectrometry. Expected mass shifts on susceptible amino acids to HNE modifications, including the oxyTMT label, were used to identify modified peptides by sequence database searching using PROTEINPILOT program.

At least ten peptides labeled with oxyTMT™ were identified with 99% probability in BSA-HNE-oxyTMT™ enriched sample. The unlabeled BSA (control) showed no labeled peptides (data not shown). MS/MS spectra of each labeled peptide was confirmed manually to have both oxyTMT™ reporter ion (m/z=126) and expected modification mass shifts. Factors, such as buffer pH, that might affect reactivity of the aminoxy with carbonyls were assessed, and pH 5 was selected, as well as reaction conditions using high amounts of SDS denaturant, to mimic conditions of protein isolation for membrane proteins that are prominent in enriched mitochondrial samples.

With optimized conditions for labeling and enrichment using the oxyTMT™ reagent, labeling conditions were applied in mouse liver mitochondria protein isolates labeled with HNE as exogenous sample and without HNE as endogenous sample. Western blots were performed using anti-TMT™ antibody as the primary antibody to visualize carbonylated proteins in standard protein and complex mitochondrial lysate (data not shown).

The data demonstrated oxyTMT™ as a novel solution for identification and quantification of proteins susceptible to carbonylation, providing new discoveries into the role of these modifications.

Each of the following references is expressly incorporated by reference herein in its entirety: U.S. Patent Application Publication No. 2008/0255004; U.S. Pat. Nos. 5,726,293; 5,112,951; 5,258,507; 7,001,738; and 7,932,388; Feng, J, et al (2008). Quantitative Proteomic Profiling of Muscle Type-Dependent and Age-Dependent Protein Carbonylation in Rat Skeletal Muscle Mitochondria. Journal of Gerontology; Vol. 63A, No. 11, 1137-1152; Gardner, M W & Brodbelt, J S (2010). Preferential Cleavage of N—N Hydrazone Bonds for Sequencing Bis-arylhydrazone Conjugated Peptides by Electron Transfer Dissociation. Anal. Chem. 82, 5751-5759; Kidd, D, et al (2001). Profiling Serine Hydrolase Activities in Complex Proteomes. Biochemistry, 40, 4005-4015; Muller, D. R. et al. (2001). Isotope-tagged crosslinking reagents. A new tool in mass spectrometric protein interaction analysis. *Anal. Chem.* 73, 1927-1934. Pichler P, et al. (2010). Peptide labeling with isobaric tags yields higher identification rates using iTRAQ 4-plex compared to TMT 6-plex and iTRAQ 8-plex on LTQ Orbitrap. Anal Chem. 2010 Aug. 1; 82(15):6549-58; Tang, X & Bruce, J E (2009). Chemical Cross-Linking for Protein-Protein Interaction Studies. Methods in Molecular Biology 492, 283-293; Wu, S-L, et al (2009). Mass Spectrometric Determination of Disulfide Linkages in Recombinant Therapeutic Proteins Using On-line LC-MS with Electron Transfer Dissociation (ETD). Anal Chem. 2009 Jan. 1; 81(1): 112-122. Xu, G & Chance, M R (2007). Hydroxyl Radical-Mediated Modification of Proteins as Probes for Structural Proteomics. Chem. Rev. 107, 3514-3543.

Applicants incorporate by reference the material contained in the accompanying computer readable Sequence Listing identified as Sequence_Listing_ST25.txt, having a file creation date of Mar. 8, 2013, 2:50 μm, and a file size of 893 bytes.

The embodiments described in the specification are only specific embodiments of the inventors who are skilled in the art and are not limiting. Therefore, various changes, modifications, or alterations to those embodiments may be made without departing from the spirit of the invention or the scope of the following claims.

What is claimed is:

1. A method for labeling and selective enrichment of a biomolecule in a sample, the method comprising (a) covalently tagging a biomolecule in the sample with at least one chemical affinity tag selected from a dimethyl piperidine-(DMP-) based chemical affinity tag and salts thereof, under conditions to result in a chemically tagged biomolecule (b) selectively capturing the chemically tagged biomolecule with either
  (i) a solid support to which a chemical affinity tag epitope-selective antibody is attached,
  or
  (ii) a solution comprising a chemical affinity tag epitope-selective antibody, and thereafter contacting the solution with a solid support capable of capturing the chemical affinity tag epitope-selective antibody,
to selectively capture the chemically tagged biomolecule, and (c) eluting the chemically tagged biomolecule by adding at least one elution reagent comprising at least one displacement molecule to the solid support to competitively elute under native conditions an intact chemically affinity tagged biomolecule, wherein the at least one displacement molecule is selected from the group consisting of piperidine, cis-2,6-dimethyl piperidine, 2-S-methyl piperidine, 2-methyl piperidine, 2,2,4,4-tetramethyl piperidine, N,N-diisopropylethylamine (DIPEA), and combinations thereof.

2. The method of claim 1 where step (a) is performed on a single sample or is performed on at least two separate samples and the separate samples are combined prior to step (b) resulting in a multiplex method.

3. The method of claim 1 where the chemical affinity tag is a DMP-based chemical affinity tag, having the structure

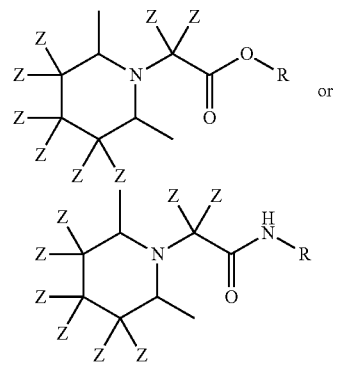

or where R is any length linker comprised of C, N, O, H between the N-substituted ring and the reactive group(s);
and where each Z is independently hydrogen, fluorine, chlorine, bromine, iodine, an amino acid side chain, a straight chain or branched $C_1$-$C_6$ alkyl group that may optionally contain a substituted or unsubstituted aryl group wherein the carbon atoms of the alkyl and aryl groups each independently comprise hydrogen or fluorine atoms, a straight chain or branched $C_1$-$C_6$ alkyl ether group that may optionally contain a substituted or unsubstituted aryl group wherein the carbon atoms of the alkyl and aryl groups each independently comprise hydrogen or fluorine atoms or a straight chain or branched $C_1$-$C_6$ alkoxy group that may optionally contain a substituted or unsubstituted aryl group wherein the carbon atoms of the alkyl and aryl groups each independently comprise hydrogen or fluorine atoms.

4. The method of claim 1 where the DMP-based chemical affinity tag is selected from the group consisting of

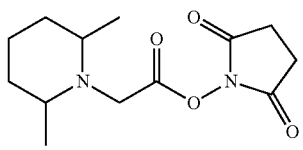

DMP-NHS

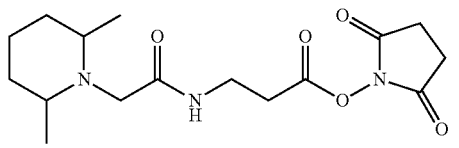

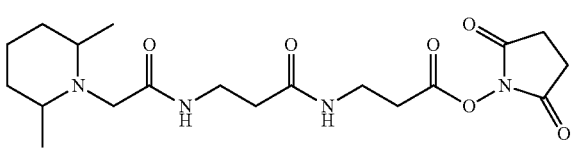

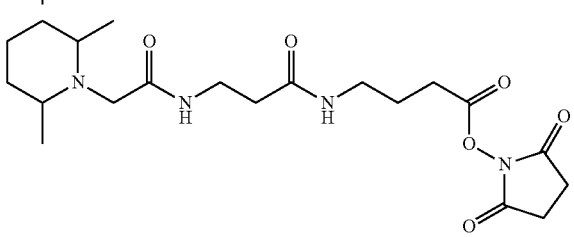

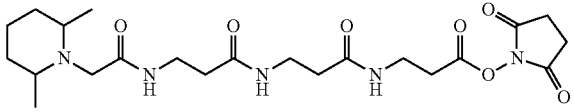

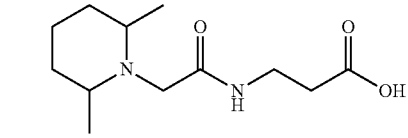

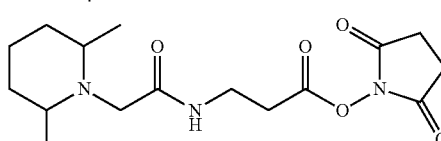

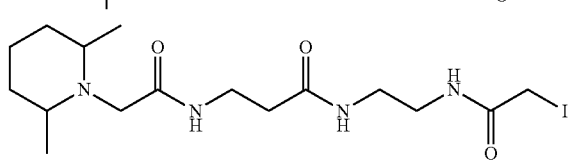

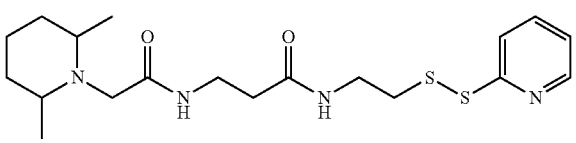

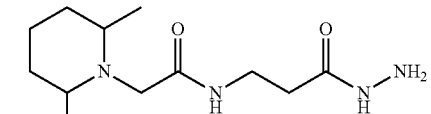

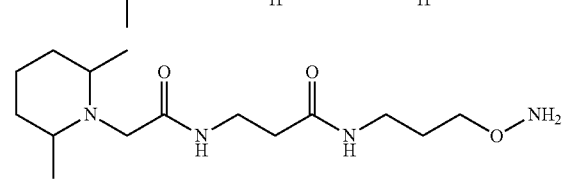

27
-continued

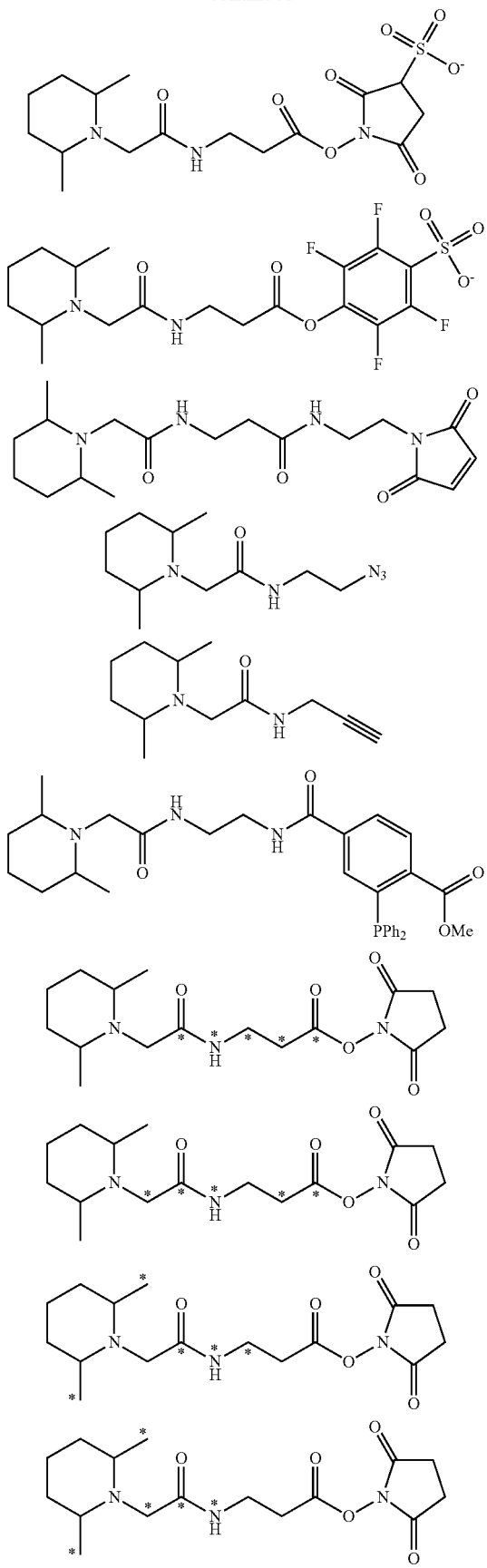

28
-continued

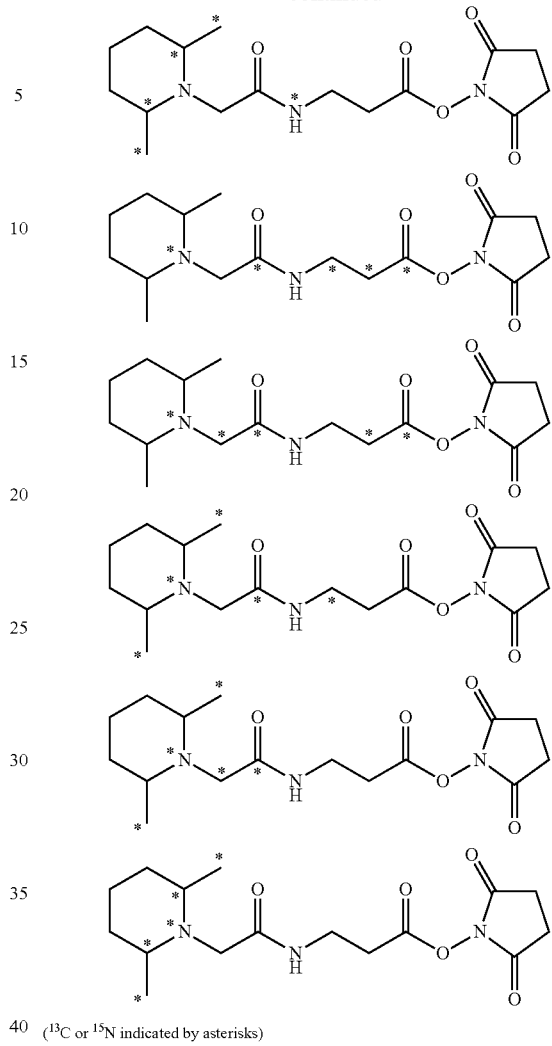

($^{13}$C or $^{15}$N indicated by asterisks)

and salts thereof, where the DMP-based chemical affinity tag is optionally isotopically labeled.

5. The method of claim 1 where the chemical affinity tag further comprises a linking group and a reactive group(s), where the chemical affinity tag labels the biomolecule by at least one of amine, carboxyl, thiol, carbonyl (aldehyde/ketone), azide, alkyne, cyclic alkyne, and/or phosphine reactive chemistries.

6. The method of claim 1 further comprising, after step (c), (d) removing the at least one elution reagent by vacuum drying, desalting with dialysis, reversed phase chromatography, or size exclusion chromatography.

7. The method of claim 1 where the biomolecule is at least one of cells, proteins, peptides, glycans, steroids, nucleotides, sugars, toxins, lipids, and/or small metabolites.

8. The method of claim 1 where the chemical affinity tag epitope-selective antibody in step (b) comprises glycoforms or Fab fragments.

9. The method of claim 1 where the epitope in step (b) comprises a fragment or substructure of the chemical affinity tag.

10. The method of claim 1 where the chemical affinity tag added in step (a) comprises an optional crosslinker.

11. The method of claim 1 further comprising after step (c) or claim 6 further comprising after step (d), performing mass spectroscopy analysis on the eluted biomolecule.

12. The method of claim 1 wherein the solid support in step (b) is either a particle that is optionally magnetic, or a surface that is at least one of plastic, glass, ceramics, silicone, metal, cellulose, or gel.

13. The method of claim 1 further comprising adding at least a second chemical affinity tag to the sample, where the at least second chemical affinity tag is different from the at least one chemical affinity tag.

14. The method of claim 1 where step (c) is performed at a pH of 4 to 10.

15. The method of claim 1 where the dimethyl piperidine-(DMP-) based chemical affinity tag is a free base or any salt thereof.

16. The method of claim 1 using an elution reagent containing at least one buffer.

17. The method of claim 16 where the buffer is selected from the group consisting of triethylammonium bicarbonate (TEAB), triethylammonium acetate (TEAA), ((hydroxymethyl)aminomethane) (Tris), 4-(2-hydroxyethyl)-1-piperazineethanesulfonic acid (HEPES), 2-[[1,3-dihydroxy-2-(hydroxymethyl)propan-2-yl]amino]ethanesulfonic acid (TES), phosphate, 2-(N-morpholino)ethanesulfonic acid (MES), 3-morpholinopropane-1-sulfonic acid (MOPS), 1,4-piperazinediethanesulfonic acid (PIPES), bicarbonate, carbonate, N-(2-hydroxy-1,1-bis(hydroxymethyl)ethyl)glycine (tricine), N,N-(bis(2-hydroxyethyl)glycine (bicine), and combinations thereof.

18. The method of claim 1 wherein the at least one chemical affinity tag of step (a) is selected from the group consisting of

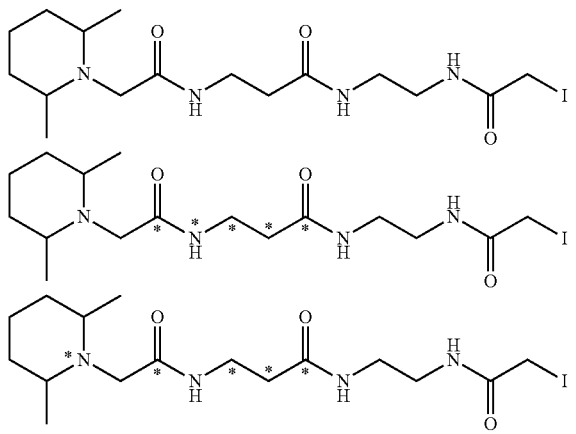

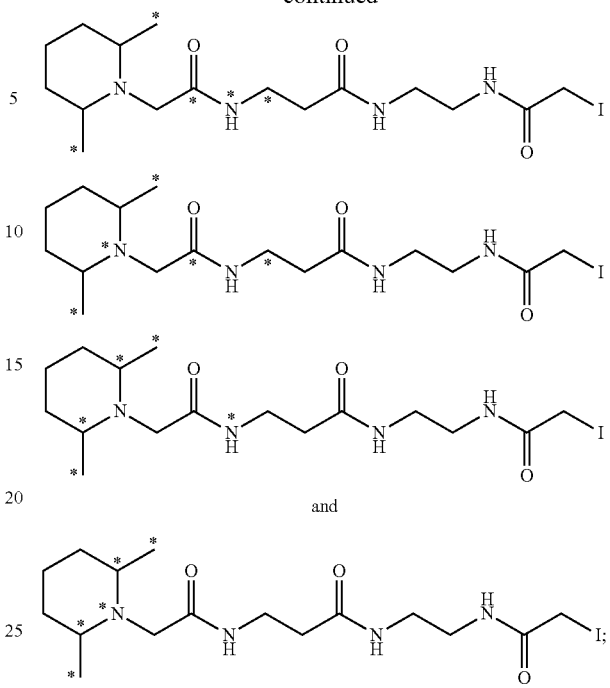

the biomolecule in the sample is at least one S-nitrosylated peptide with S-nitrosyl groups reduced to generate free sulfhydryl groups prior to step (a), the free sulfhydryl groups are reactive with the at least one chemical affinity tag to chemically tag the biomolecule.

19. The method of claim 18 wherein the sample is a plurality of blood serum samples; after covalently tagging the biomolecule in each of the samples in step (a), the samples are combined prior to step (b); and following step (c), performing mass spectroscopy analysis on the eluted biomolecule for a relative quantitation of peptides in a single MS analysis.

20. The method of claim 19, wherein the sample is subjected to abundant serum protein depletion prior to covalently tagging the biomolecule in each of the samples.

21. The method of claim 1, wherein the at least one elution reagent further comprises triethylamine (TEA), triethylammonium bicarbonate (TEAB) or triethylammonium acetate (TEAA).

* * * * *

SEQUENCE LISTING

```
<160> NUMBER OF SEQ ID NOS: 2

<210> SEQ ID NO 1
<211> LENGTH: 17
<212> TYPE: PRT
<213> ORGANISM: Artificial Sequence
<220> FEATURE:
<223> OTHER INFORMATION: S-nitrosylated peptides
<220> FEATURE:
<221> NAME/KEY: MISC_FEATURE
<222> LOCATION: (14)..(14)
<223> OTHER INFORMATION: iodoTMT labeling

<400> SEQUENCE: 1

Gly Cys Ile Thr Ile Ile Gly Gly Gly Asp Thr Ala Thr Cys Cys Ala
1               5                   10                  15

Lys

<210> SEQ ID NO 2
<211> LENGTH: 8
<212> TYPE: PRT
<213> ORGANISM: Artificial Sequence
<220> FEATURE:
<223> OTHER INFORMATION: S-nitrosylated peptides
<220> FEATURE:
<221> NAME/KEY: MISC_FEATURE
<222> LOCATION: (1)..(1)
<223> OTHER INFORMATION: iodoTMT labeling

<400> SEQUENCE: 2

Cys Met Met Ala Gln Tyr Asn Arg
1               5
```